United States Patent
Barkol et al.

(10) Patent No.: US 11,545,271 B2
(45) Date of Patent: Jan. 3, 2023

(54) SYSTEMS AND METHODS FOR PUBLIC AND PRIVATE COMMUNICATION THREADS

(71) Applicant: GE Precision Healthcare LLC, Milwaukee, WI (US)

(72) Inventors: Omer Barkol, Haifa (IL); Andreas Tzanetakis, Madison, WI (US); Michelle Townshend, Traverse City, MI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 331 days.

(21) Appl. No.: 16/546,217

(22) Filed: Aug. 20, 2019

(65) Prior Publication Data

US 2021/0057111 A1 Feb. 25, 2021

(51) Int. Cl.
| | |
|---|---|
| *G16H 80/00* | (2018.01) |
| *G16H 10/60* | (2018.01) |
| *G06F 21/62* | (2013.01) |
| *H04L 51/00* | (2022.01) |
| *G06F 3/0482* | (2013.01) |
| *H04L 51/046* | (2022.01) |

(Continued)

(52) U.S. Cl.
CPC ........... *G16H 80/00* (2018.01); *G06F 3/0482* (2013.01); *G06F 9/451* (2018.02); *G06F 21/6245* (2013.01); *G16H 10/60* (2018.01); *H04L 51/046* (2013.01); *H04L 51/16* (2013.01)

(58) Field of Classification Search
CPC .... G06F 3/0482; G06F 9/451; G06F 21/6245; G16H 80/00; G16H 10/60; H04L 51/046; H04L 51/16
See application file for complete search history.

(56) References Cited

U.S. PATENT DOCUMENTS

| | | | | |
|---|---|---|---|---|
| 4,829,294 A | * | 5/1989 | Iwami | G09G 5/14 715/204 |
| 4,962,475 A | * | 10/1990 | Hernandez | G09G 5/14 345/686 |
| 5,357,427 A | | 10/1994 | Langen et al. | |

(Continued)

OTHER PUBLICATIONS

Beyond Patient Monitoring: Conversational Agents Role in Telemedicine & Healthcare Support for Home-Living Elderly Individuals Ahmed Fadhil [v1] Sat, Mar. 3, 2018 13:45:08 UTC (Year: 2018).*

(Continued)

*Primary Examiner* — Nicholas Augustine

(57) ABSTRACT

Systems and methods are provided for collaborative communication between a virtual healthcare assistant and a plurality of care providers. In one example, a system includes a display and a computing device operably coupled to the display and storing instructions executable to output, to the display, a public communication thread including communication among two or more care providers monitoring a patient and a virtual healthcare assistant, the public communication thread specific to the patient and responsive to a request from a first care provider of the two or more care providers, output, to the display, a private communication thread including communication only between the first care provider and the virtual healthcare assistant, the private communication thread specific to the patient.

16 Claims, 14 Drawing Sheets

(51) Int. Cl.
*G06F 9/451* (2018.01)
*G06F 3/00* (2006.01)

(56) References Cited

U.S. PATENT DOCUMENTS

| | | | | |
|---|---|---|---|---|
| 5,367,619 | A * | 11/1994 | Dipaolo | G06F 8/38 715/825 |
| 5,640,577 | A * | 6/1997 | Scharmer | G06F 40/174 715/808 |
| 5,823,948 | A * | 10/1998 | Ross, Jr. | G16H 10/60 600/300 |
| 5,845,255 | A * | 12/1998 | Mayaud | G06Q 40/08 705/3 |
| 5,963,952 | A * | 10/1999 | Smith | G06F 40/123 707/999.102 |
| 6,006,240 | A * | 12/1999 | Handley | G06V 30/412 715/220 |
| 6,192,380 | B1 * | 2/2001 | Light | G06F 40/174 707/999.009 |
| 6,910,179 | B1 * | 6/2005 | Pennell | G06Q 20/108 705/26.8 |
| 6,981,001 | B1 * | 12/2005 | Reddick | G16H 40/20 |
| 10,809,876 | B2 * | 10/2020 | Brown | G06Q 50/20 |
| 2001/0034615 | A1 | 10/2001 | Wilkinson et al. | |
| 2006/0010098 | A1 * | 1/2006 | Goodnow | G06F 13/4068 |
| 2006/0265249 | A1 * | 11/2006 | Follis | G16H 10/60 715/254 |
| 2008/0244453 | A1 * | 10/2008 | Cater | G06F 3/04817 715/835 |
| 2011/0125528 | A1 * | 5/2011 | Padate | G16H 10/60 705/3 |
| 2013/0325493 | A1 * | 12/2013 | Wong | G16Z 99/00 705/2 |
| 2015/0154721 | A1 | 6/2015 | Thompson | |
| 2018/0068082 | A1 * | 3/2018 | Brown | G10L 15/22 |
| 2018/0197624 | A1 * | 7/2018 | Robaina | G06F 16/2379 |
| 2019/0130915 | A1 * | 5/2019 | Nitz | G10L 15/32 |
| 2019/0341145 | A1 * | 11/2019 | Prakash | G16H 50/20 |

OTHER PUBLICATIONS

Pblcloud Virtual Patient Simulator: Enhancing Immersion Through Natural Language Processing—Yale University School of Medicine Mar. 7, 2017 (Year: 2017).*

"See the Kore.ai Healthcare Bots Come to Life," YouTube Website, Available Online at https://www.youtube.com/watch?v=FZiqokBtGzk&feature=youtu.be, Mar. 22, 2017, 3 pages.

Durgampudi, K., "AI is spawning new models of care, not just cars," Nuance Website, Available Online at https://whatsnext.nuance.co.uk/healthcare/ai-in-medicine-reshaping-patient-clinicians-care/, Available as Early as Apr. 25, 2017, 5 pages.

"Enterprise Digital Collaboration Software," eXo Website, Available Online at https://www.exoplatform.com/collaboration-software-tour/#popup1, Available as Early as Jul. 9, 2017, 13 pages.

"Microsoft Healthcare Bot," Microsoft Website, Available Online at https://www.microsoft.com/en-us/research/project/health-bot/. Available as Early as Dec. 14, 2017, 8 pages.

Pennic, J., "Kyruus Integrates With IBM Watson for AI-Assisted Patient-Provider Matching & Scheduling," HIT Consultant Website, Available Online at https://hitconsultant.net/2018/03/05/kyruus-ibm-watson-ai-patient-provider-matching/#.XdMG_NVKhGp, Mar. 5, 2018, 6 pages.

Carter, S., "How Chatbots and AI are Changing the Healthcare Industry," ScienceSoft Website, Available Online at https://www.scnsoft.com/blog/how-chatbots-and-ai-are-changing-the-healthcare-industry, May 27, 2018, 8 pages.

Houlding, D., "Improve patient engagement and efficiency with AI powered chatbots," Microsoft Azure Website, Available Online at https://azure.microsoft.com/en-in/blog/improve-patient-engagement-and-efficiency-with-ai-powered-chatbots/, Sep. 19, 2018, 6 pages.

"Philips Launches First Global Start-Up Collaboration Program Focused on the Application of Artificial Intelligence in Healthcare," Philips Website, Available Online at http://www.ehealthnews.eu/philips/5654-philips-launches-first-global-start-up-collaboration-program-focused-on-the-application-of-artificial-intelligence-in-healthcare, Oct. 17, 2018, 5 pages.

Arndt, R., "Healthcare providers are teaming with chatbots to assist patients," Modern Healthcare Website, Available Online at https://www.modernhealthcare.com/article/20181208/TRANSFORMATION01/181209977/healthcare-providers-are-teaming-with-chatbots-to-assist-patients, Dec. 8, 2018, 12 pages.

"Ascom Unite Collaborate: Enable patient-centric communication for care teams," Ascom Website, Available Online at https://www.ascom.com/products/category/smartphone-applications/unite-collaborate.html, Available Online as Early as Jan. 1, 2019, 9 pages.

"Influence of Chatbots and AI to the Healthcare Industry," CABOT Solutions Website, Available Online at https://www.cabotsolutions.com/influence-of-chatbots-and-ai-to-the-healthcare-industry, Jan. 14, 2019, 13 pages.

"Personalized Care: Chatbots Trigger Innovation in Healthcare," Kore.ai Website, Available Online at http://kore.ai/solutions/industries/healthcare/, Available as Early as May 22, 2019, 6 pages.

"Enterprise Collaboration Platform," eXo Website, Available Online at https://www.exoplatform.com/digital-collaboration-platform/, Available as Early as Jul. 29, 2019, 7 pages.

Wiggers, K., "Microsoft Healthcare Bot Service becomes generally available in Azure Marketplace," Venture Beat Website, Available Online at https://venturebeat.com/2019/02/07/microsofts-healthcare-bot-service-becomes-generally-available-in-azure-marketplace/, Feb. 7, 2019, 5 pages.

* cited by examiner

SYSTEMS AND METHODS FOR PUBLIC AND PRIVATE COMMUNICATION THREADS

FIELD

Embodiments of the subject matter disclosed herein relate to user interfaces for public and private communication threads, and for collaborative communication among a virtual healthcare assistant and a plurality of care providers via the public and private communication threads.

BACKGROUND

Acute care of patients in a hospital or other medical facility may be carried out with multiple care providers per patient and may include multiple patient monitoring devices monitoring each patient. Thus, to ensure a rapid response should a patient's condition deteriorate, near-continuous monitoring of the output from the multiple monitoring devices may be necessary. Further, coordination of patient care among all the care providers may be complicated or time-consuming, further stretching care provider resources. Additionally, the presentation of patient medical information to the care providers may require multiple time-consuming and cumbersome requests or searches for information.

BRIEF DESCRIPTION

In one embodiment, a system includes a display and a computing device operably coupled to the display and storing instructions executable to output, to the display, a public communication thread including communication among two or more care providers monitoring a patient and a virtual healthcare assistant, the public communication thread specific to the patient and responsive to a request from a first care provider of the two or more care providers, output, to the display, a private communication thread including communication only between the first care provider and the virtual healthcare assistant, the private communication thread specific to the patient.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
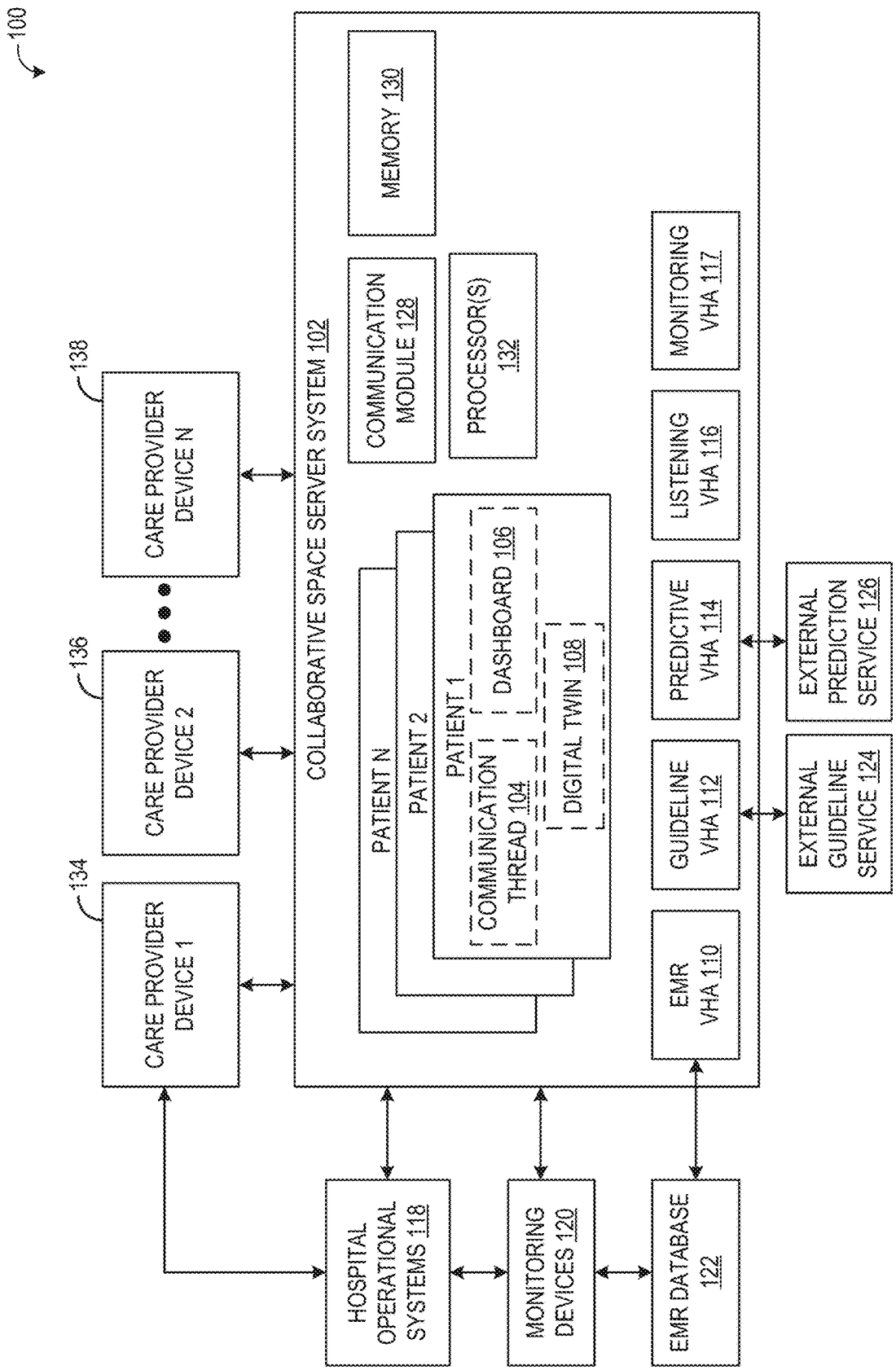
FIG. 1 schematically shows an example collaborative healthcare system.

The following description relates to various embodiments of a collaborative healthcare system that facilitates communication among care providers of a patient (which may be collectively referred to as a care provider team or care team) and also utilizes machine and/or other deep learning models (e.g., in the form of virtual healthcare assistants) to perform certain patient monitoring and diagnostic activities. The collaborative healthcare system includes patient-specific communication channels that include communication thread-dashboard pairs to facilitate communication among the care providers and virtual healthcare assistants (also referred to as bots) on the communication thread while also graphically providing relevant patient care information (current vital signs, trends, medical history, etc.) to the care providers via the dashboard and/or communication thread.

The virtual healthcare assistants may function as information retrievers, data monitors, predictors, and more to assist the care providers. The virtual healthcare assistants may provide requested patient data (e.g., fetch data from an electronic medical record), detect changes in patient state and alert the care providers of the changed state (e.g., by detecting that a patient vital sign has reached a condition relative to a threshold), and provide care guidelines, suggested diagnostic tests, and diagnoses to the care providers. The virtual healthcare assistants may be trained to communicate using natural language including medical language, thereby allowing for care providers to communicate with the virtual healthcare assistants in the same manner as other care providers.

Each communication channel may be specific to a given patient in a given acute care facility or other medical facility or healthcare setting (e.g., hospital, urgent care facility, or nursing home). A communication channel may be initiated upon admission of the patient to the medical facility. Each care provider of the patient may be joined to the communication channel, thereby allowing collaboration and communication among all care providers (e.g., doctors, nurses, and/or specialists such as radiologists) of the patient. The one or more virtual healthcare assistants may also be joined to the communication channel. Communication occurring on the communication channel may be in the form of text messages, rich media, and/or other forms, thereby allowing care providers to view graphs of patient medical trends, medical images, and so forth. Messages sent and received on the communication channel may be saved at a central location as a communication thread, allowing care providers to access prior conversations on the channel. For example, if a virtual healthcare assistant detects a change in a patient condition that indicates potential health issues, such as high blood pressure, the virtual healthcare assistant may note the high blood pressure and alert the care provider(s) via the communication thread. The blood pressure may be displayed via the patient dashboard along with the alert. A care provider may view the blood pressure measurement by selecting the alert in the communication thread. Later, the care provider may select a graphical display of the alert in the dashboard in order to launch the portion of the communication thread in which the blood pressure alert was issued.

The dashboard and communication thread may be viewable from a variety of client devices, including but not limited to a provider client device (such as a monitor in a nurse's station) and a provider mobile device (such as a tablet or smart phone). Thus, care providers may have access to relevant data and assistance from the virtual healthcare assistants from virtually any allowed location within the medical facility, and even off-site locations in some examples.

Further, the patient-specific communication channels of the collaborative healthcare system described herein may include both public communication threads (as described above) and private communication threads. A patient-specific private communication thread may include messages and/or relevant medical information sent between a single care provider and only the one or more virtual healthcare assistants, without including any of the other care providers that are a part of the patient's care team. The public channel is aimed to allow the care team to collaborate by sending patient-centric messages to one another, in addition to the virtual healthcare assistant(s), which is also involved in this collaboration and may provide the care team information that is indicated for patient care. In contrast, the private channel may allow a care provider to request personal assistance (such as "remind me to take vitals in 20 minutes"), personal education (such as "what is the sepsis bundle?"), or any other assistance that the care provider may prefer to receive privately (such as asking "what is the blood pressure trend?" after being notified from another care provider that blood pressure is dropping, not wanting to look untrusting). In some examples, patient information may first be retrieved in the private channel and may be brought to the care team's attention by "publishing" the patient information into the public communication thread upon a request from the care provider on the private communication thread. This mechanism of publishing gives the full flexibility to the care provider to first ask a question privately (e.g. "what is the blood pressure trend?") but then, if encountered with information that appears to be relevant to the care team as a whole, publish the information into the public communication thread.

Figure 2:
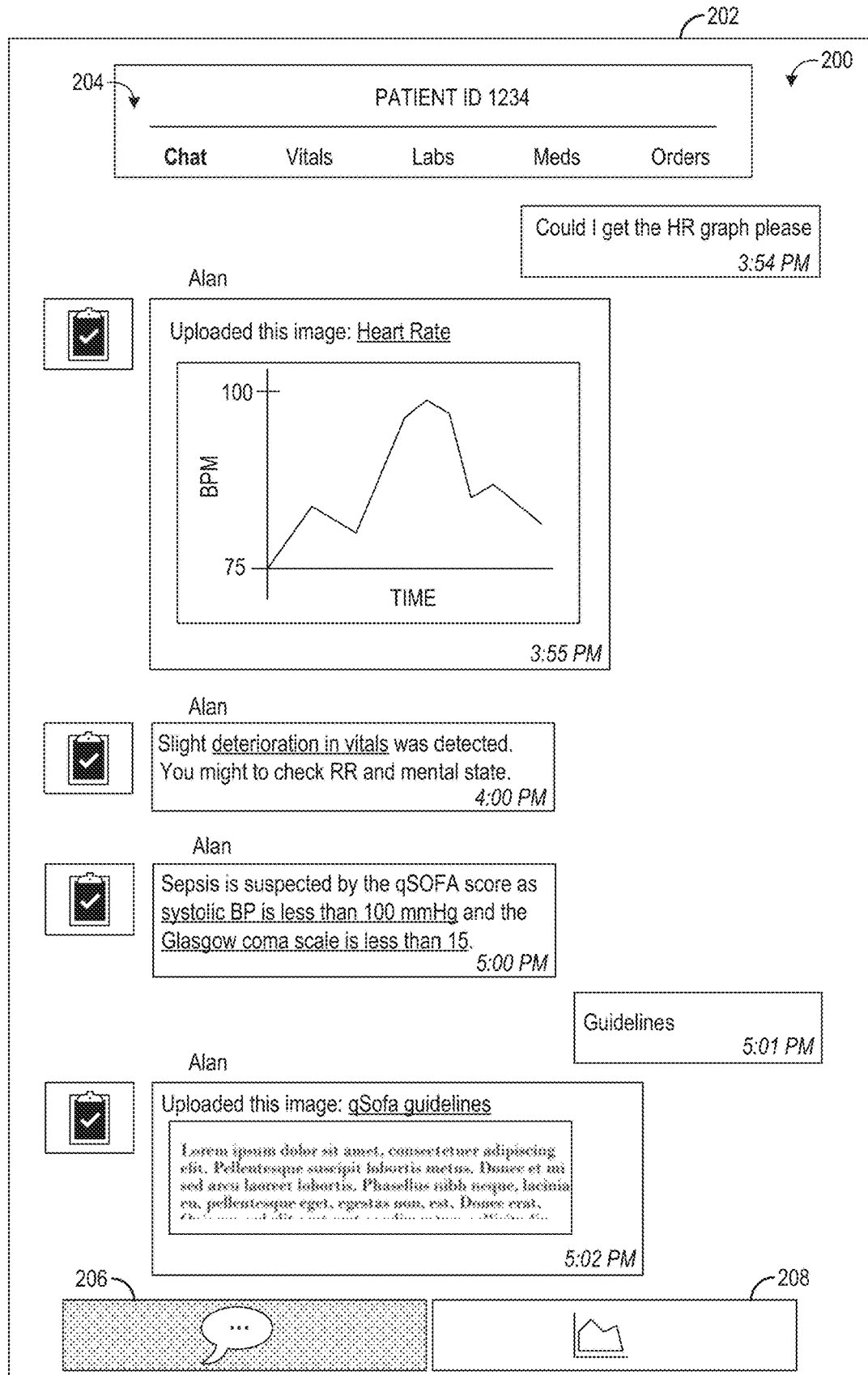
FIG. 2 shows an example display device displaying a communication thread occurring on a communication channel of the collaborative healthcare system.
Figure 3:
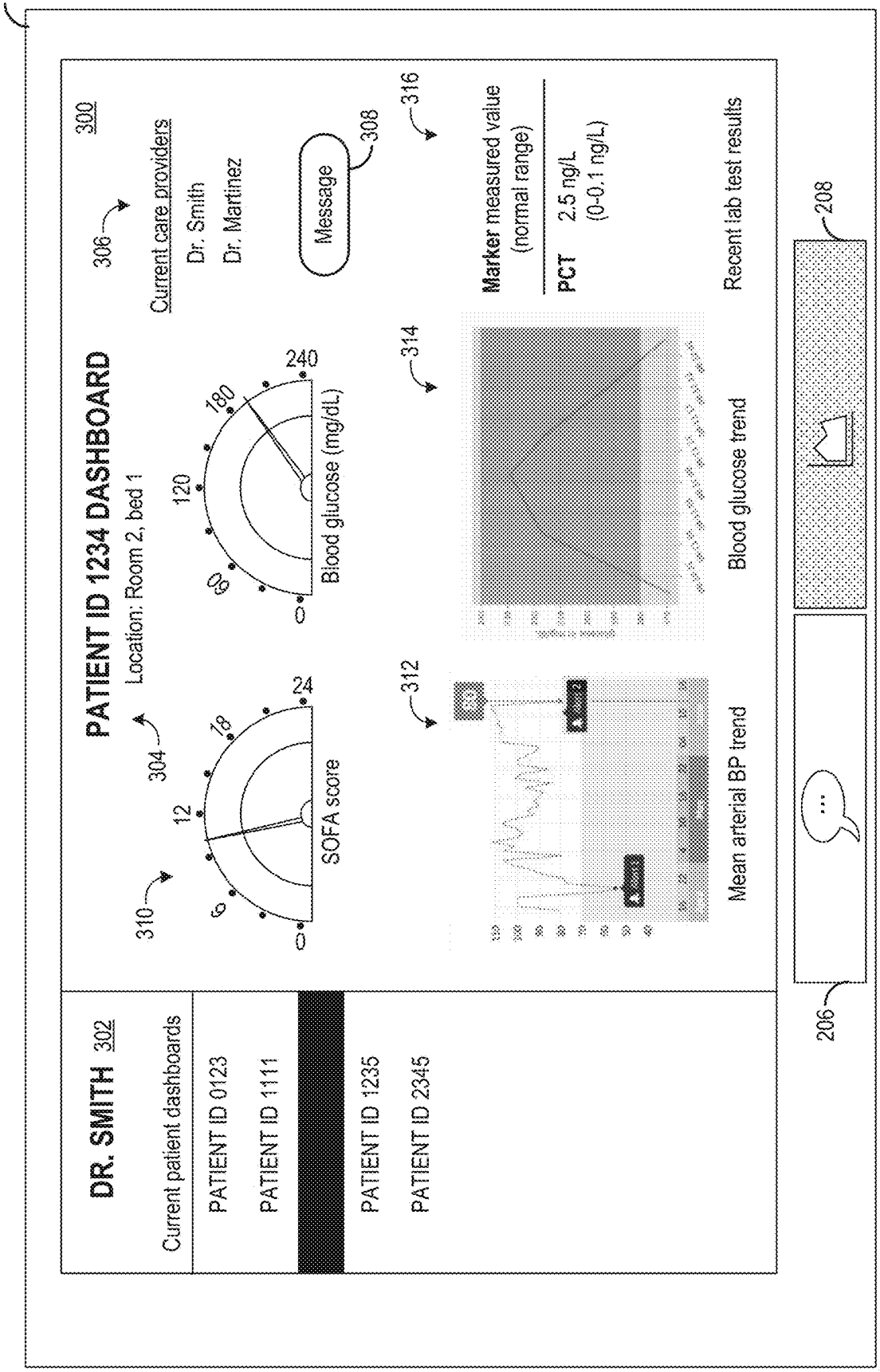
FIG. 3 shows an example display device displaying a dashboard of the collaborative healthcare system.
Figure 4:
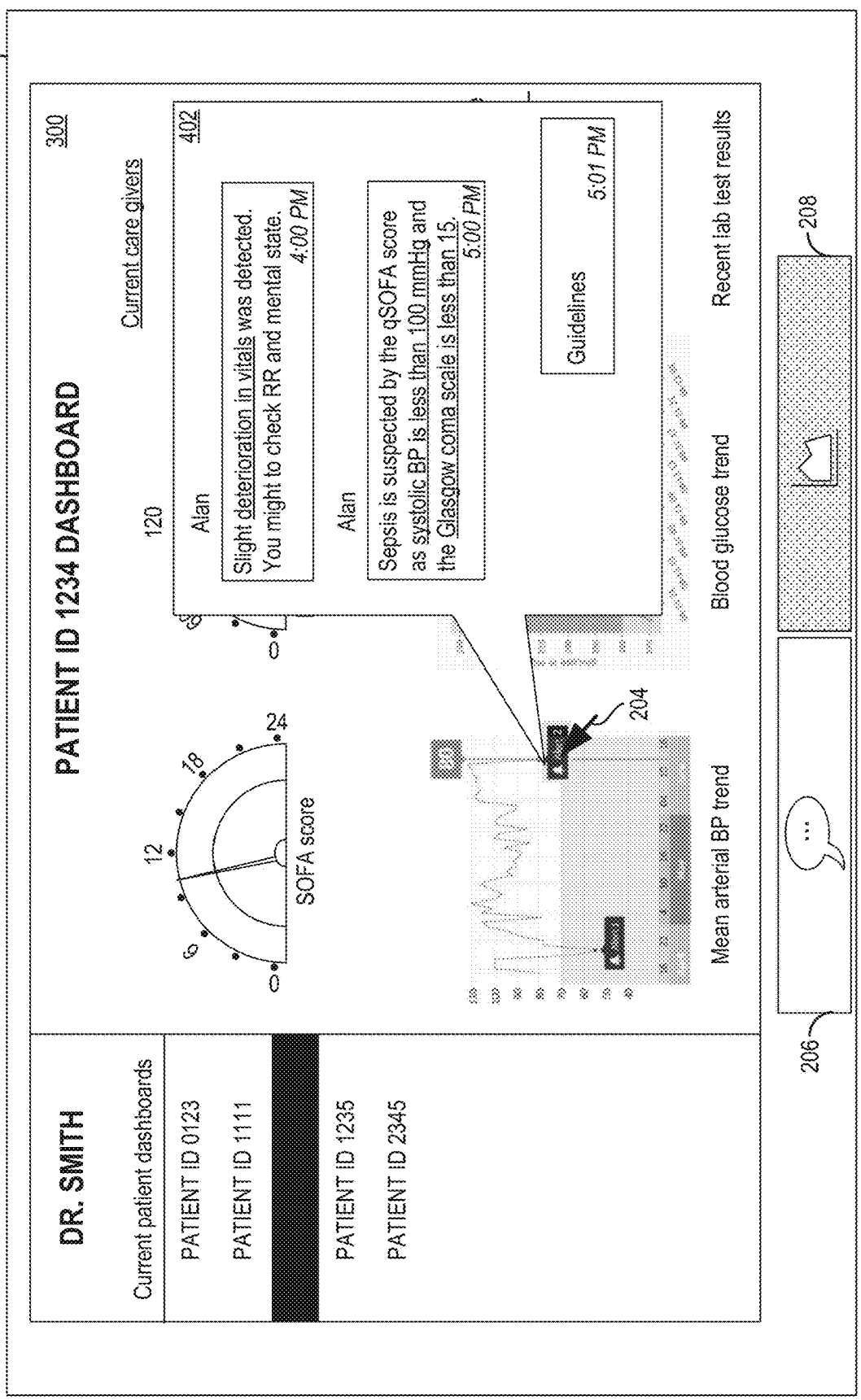
FIG. 4 shows an example display device displaying the dashboard of FIG. 3 including display of a portion of the communication thread of FIG. 2.
Figure 5:
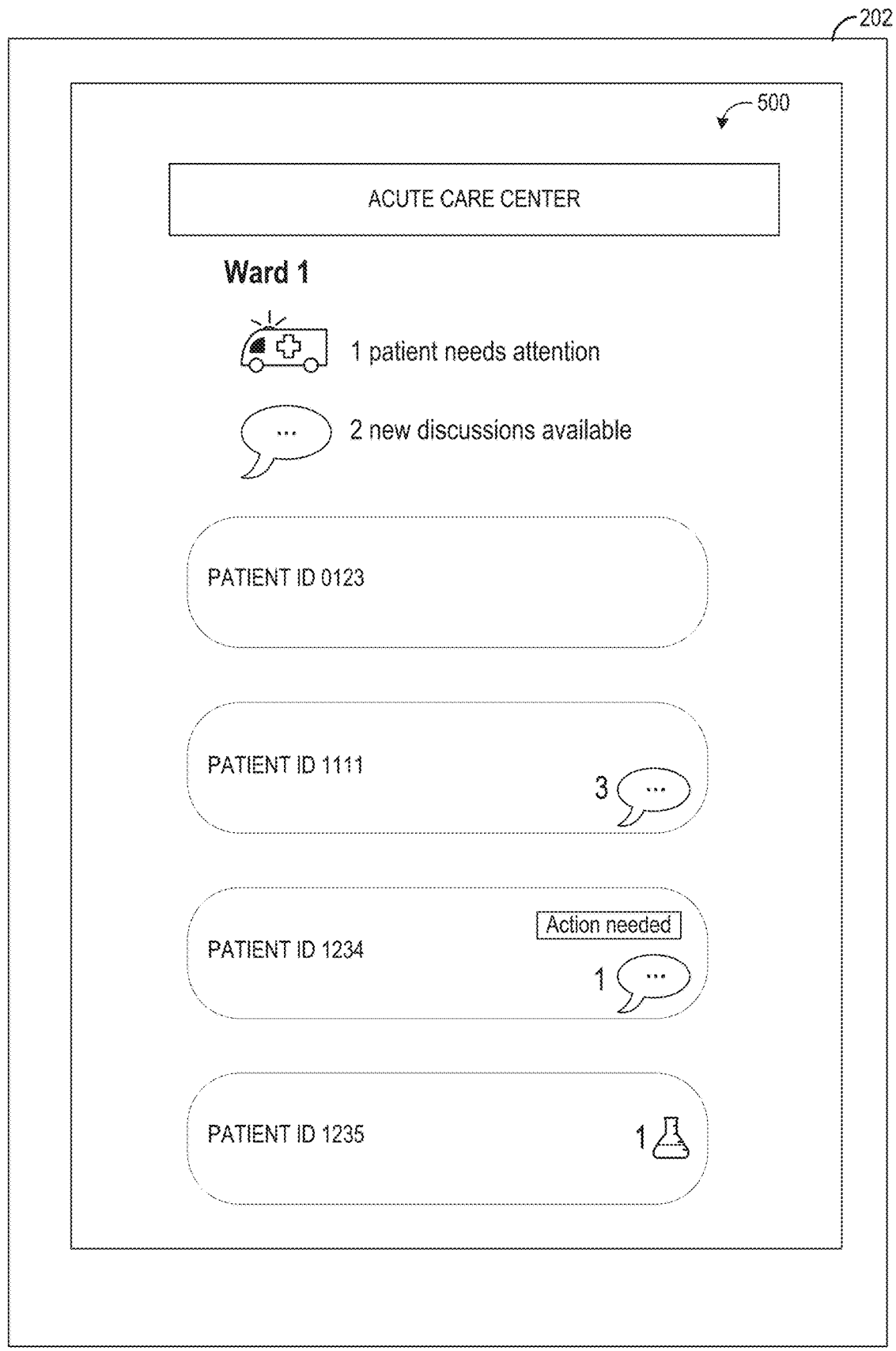
FIG. 5 shows an example display device displaying a collaborative interface.
Figure 6:
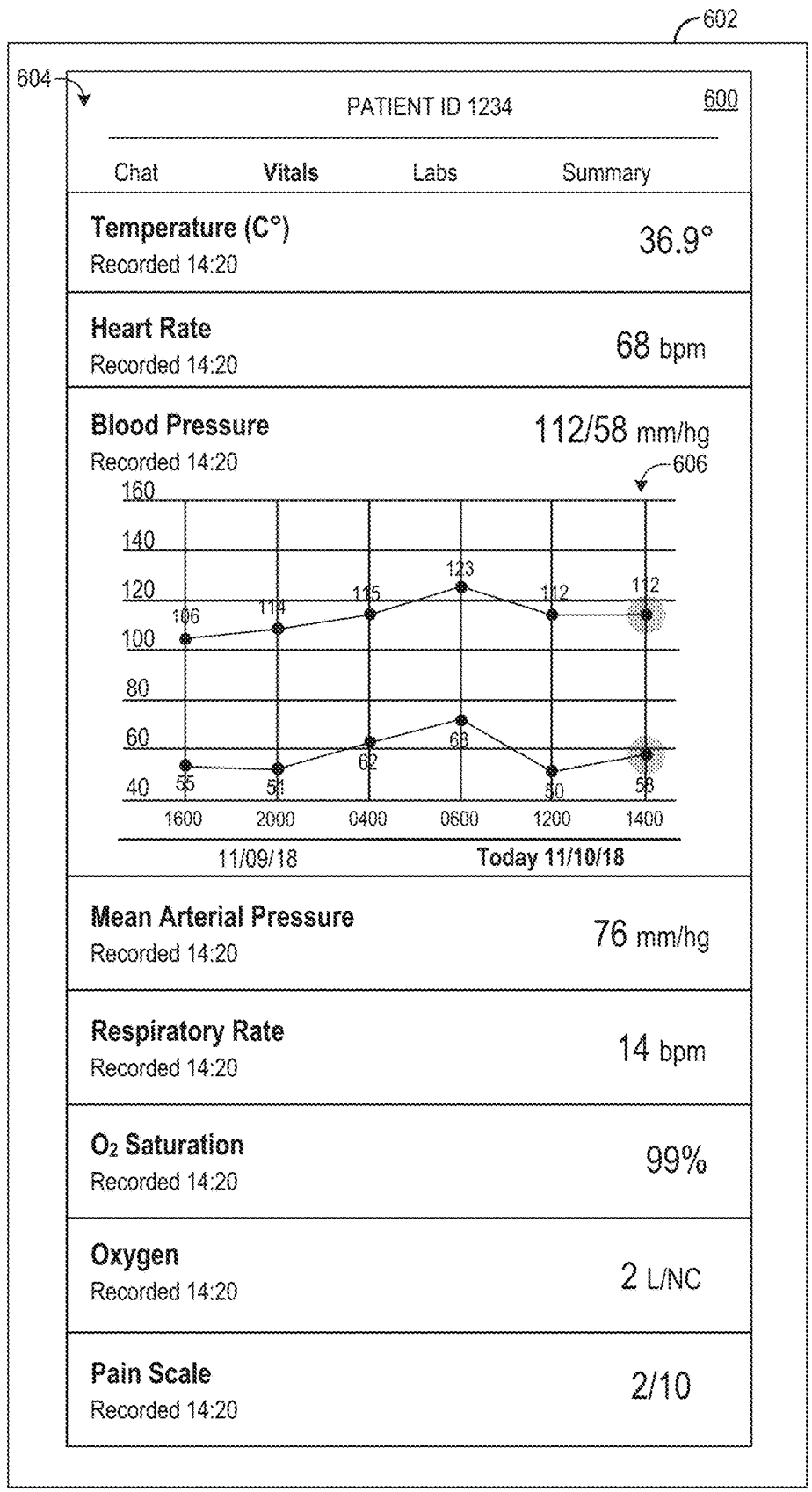
FIG. 6 shows an example display device displaying another example dashboard of the collaborative healthcare system.

An example collaborative healthcare system is shown in FIG. 1. The collaborative healthcare system may be included in or associated with a medical facility and may include a communication channel comprising a communication thread (which may include a public communication thread and, upon request, a private communication thread) and a dashboard for each admitted patient of the medical facility. The collaborative healthcare system may further include one or more virtual healthcare assistants. Communication may occur on a communication channel in the form of one or more communication threads (e.g., of text and/or rich media messages) between care providers of the patient and the one or more virtual healthcare assistants, as shown in FIG. 2 as well as FIGS. 7-11. Patient-specific medical information may be displayed to the care providers and/or other users via a dashboard. As shown in FIG. 3, the dashboard may be launched in response to a first selection of a link on the communication thread. The dashboard may be configured to display alerts output by the one or more virtual healthcare assistants, and the alerts may be selectable to launch a portion of the communication thread occurring on the communication channel, as shown in FIG. 4, or a full version of the communication thread. Additionally, a preview of the dashboard may be launched in response to a second selection of a link on the communication thread. Further, a collaborative system interface, as shown in FIG. 5, may be displayed on a suitable display device in order to allow a user to select a communication channel or dashboard to view. In some examples, the dashboard may take on a different visual form, as shown in FIG. 6, and a user may navigate between the dashboard and communication thread using a menu. The communication thread-dashboard pairs may be generated and accessed according to the method illustrated in FIG. 12. Public and private communication threads for a given patient may be generated and displayed according to the method of FIG. 13 and may be visually depicted over time via an analytics interface as shown in FIG. 14.

FIG. 1 schematically shows an example collaborative healthcare system 100 that may be implemented in medical facility such as a hospital. Collaborative healthcare system 100 may include a collaborative space server system 102. Server system 102 may include resources (e.g., memory 130, processor(s) 132) that may be allocated to store and execute one or more communication threads, a dashboard, and a digital twin for each of a plurality of patients. For example, as shown in FIG. 1, a communication thread 104, dashboard 106, and digital twin 108 are stored on server system 102 for a first patient (patient 1); a plurality of additional communication threads, dashboards, and digital twins may be stored on server system 102, each corresponding to a respective patient (patient 2 up to patient N).

As explained above, the communication thread 104 may facilitate communication among a care provider team (which may include multiple care providers that are each providing care to the patient (e.g., patient 1)) as well as one or more virtual healthcare assistants (explained in more detail below). Messages sent on the communication thread 104 may be saved and may be accessible via the dashboard 106 (and the dashboard may be accessible via the communication thread). Further, the patient medical information, including medical history, current state, vital signs, and other information, may be entered to the digital twin 108, which may be used to gain situational awareness, clinical context, and medical history of the patient to facilitate predicted patient states, procurement of relevant treatment guidelines, patient state diagnoses, etc. In some examples, as explained in more detail below with respect to FIGS. 6-13, communication occurring via the communication thread 104 may occur over two threads: a private thread and a public thread. The private thread may include communication only between a single care provider and the one or more virtual healthcare assistants. The public thread may include communication between all care providers assigned/joined to the communication channel and the one or more virtual healthcare assistants. For example, if a care provider sends a message on the private communication thread, only the one or more virtual healthcare assistants may receive the message. When the one or more virtual healthcare assistants respond to a message sent on the private communication thread, the message sent in response by the one or more virtual healthcare assistants may only be sent to a device(s) of the care provider and may not be viewed by any other care providers. In contrast, if the care provider sends a message on the public communication thread, the one or more virtual healthcare assistants and all care providers joined to that patient's communication channel may receive the message. When the one or more virtual healthcare assistants or another care provider responds to a message sent on the public communication thread, the message sent in response may be sent to all devices of the care team.

Communication occurring on communication thread 104 may be displayed on one or more suitable display devices associated with a respective care provider device and/or medical facility administration device. Likewise, dashboard 106 may be displayed on the one or more display devices. As shown in FIG. 1, a plurality of care provider devices, from a first care provider device 134, a second care provider device 136, and on up to an nth care provider device 138, may be communicatively coupled to server system 102. Each care provider device may include a processor, memory, communication module, user input device, display (e.g., screen or monitor), and/or other subsystems and may be in the form of a desktop computing device, a laptop computing device, a tablet, a smart phone, or other device. Each care provider device may be adapted to send and receive encrypted data and display medical information, including medical images in a suitable format such as digital imaging and communications in medicine (DICOM) or other standards. The care provider devices may be located locally at the medical facility (such as in a nurses station or in the room of a patient) and/or remotely from the medical facility (such as a care provider's mobile device).

When viewing communication thread 104 and/or dashboard 106 via a display of a care provider device, a care provider may enter input (e.g., via the user input device, which may include a keyboard, mouse, microphone, touch screen, stylus, or other device) that may be processed by the care provider device and sent to the server system 102. In examples where the user input is a message to be sent to other care providers and/or one or more virtual healthcare assistants, the message may be sent to the server system 102, where the message may be saved as part of the communication thread 104 and then the server system 102 may send the message to other verified participants on the communication channel (e.g., the other care providers and/or one or more virtual healthcare assistants that are joined to the communication channel). When both public and private communication threads are created, messages sent on the public and private communication threads may be saved as part of separate communication threads. In examples where the user input is a selection of a link or user interface control button of the dashboard, the user input may trigger display of the communication thread, trigger progression to a desired state of the dashboard (e.g., trigger display of desired patient medical information), trigger updates to the configuration of the dashboard, or other actions.

The collaborative space server system 102 may be communicatively coupled to hospital operational systems 118. The hospital operational systems 118 may store and/or control a variety of hospital-, care provider-, and patient-related information, including but not limited to patient admission information (including date of admission and location of the patient within the medical facility), patient care protocols and workflows, and care provider information including which care providers are monitoring/treating which patients. Further, the hospital operational systems 118 may be communicatively coupled to a plurality of monitoring devices 120, an electronic medical records (EMR) database 122 (described in more detail below), and one or more of the care provider devices. The monitoring devices 120 may include traditional medical devices monitoring respective patients, such as pulse oximeters, heart rate monitors, blood glucose monitors, and ECGs, as well as microphones, cameras, and other devices. The monitoring devices 120 may send output directly to the server system 102 and/or may send output to the hospital operational systems 118, EMR database 122, and/or one or more care provider devices. For example, a plurality of monitoring devices monitoring patient 1 may be configured to send output to the server system 102 and the server system 102 may be configured to send some or all of the data output by the monitoring devices to a care provider device (such as care provider device 134). Further, in some examples, server system 102, hospital operational systems 118, and/or EMR database 122 may receive diagnostic imaging information obtained from one or more imaging modalities, such as ultrasound, CAT, MRI, X-ray, etc.

The hospital operational systems 118 may direct creation of and control access to each communication thread and dashboard. For example, when a patient is admitted, the hospital operational systems 118 may associate the patient with an identifier (e.g., an identification code) and notify the collaborative space server system 102 to generate a communication channel for that patient. When a care provider is assigned to assist in management/treatment of the patient, the hospital operational systems 118 may notify the collaborative space server system 102 to join that care provider to the patient's communication channel (the care provider may also be associated with an identifier which may be used to identify the care provider and appropriately distribute messages sent and received on the channel). In this way, the hospital operational systems 118 may control who has access to patient information. In some examples, hospital operational systems 118 and/or server system 102 may control levels of accessibility to patient information depending on the location of a care provider device (e.g., devices located at the medical facility may have access to more patient information than devices located remotely from the medical facility). Additional information about the hospital operational systems 118 is presented below.

Collaborative space server system 102 may further store instructions for (e.g., in memory 130) and be configured to execute (e.g., via processor(s) 132) a plurality of virtual healthcare assistants (VHAs). As shown, collaborative space server system 102 includes an electronic medical record (EMR) VHA 110, a guideline VHA 112, a predictive VHA 114, a listening VHA 116, and a monitoring VHA 117. The VHAs may be realized as several VHAs each for a different purpose, as described herein, various groups of VHAs (e.g., a the guideline VHA 112 and predictive VHA 114 may be combined into one VHA that is configured to both diagnose or predict patient state and output relevant guidelines), or as one overall VHA, which represents all the different attributes that will be hereby elaborated. All activations of VHAs by human care providers may be performed by using natural language including medical language, either by text or by voice.

EMR VHA 110 is configured to retrieve patient information from an electronic medical record database, such as EMR database 122, and present the retrieved data via the communication thread and/or dashboard. For example, a care provider may send a request to the EMR VHA 110, through the communication channel, for a particular piece of patient medical history saved in an EMR of the patient. The EMR VHA 110 may receive the request and determine, from the natural language of the text, that the piece of patient medical history has been requested. The EMR VHA 110 may obtain the piece of medical history from EMR database 122. The EMR VHA 110 may then send the piece of medical history to the care provider in the form of a message on the communication thread 104. In some examples where the requested piece of medical history is also saved in the digital twin 108, EMR VHA 110 may be configured to retrieve the medical history from the digital twin 108.

EMR database 122 may be an external database accessible by EMR VHA 110 via a secured hospital interface, or EMR database 122 may be a local database (e.g., housed on a device of the hospital). EMR database 122 may be a database stored in a mass storage device configured to communicate with secure channels (e.g., HTTPS and TLS), and store data in encrypted form. Further, the EMR mass storage device is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc.

Thus, the EMR VHA 110 serves as a connection to the EMR database. The EMR VHA may interpret questions by the human care providers regarding the patient and allows querying of the EMR database for relevant information regarding the patient (e.g. "what was the average systolic blood pressure in the last four hours?" or "show me the trend of the O2 saturation"). Queries can implicitly relate to the patient's status or medical history. The EMR VHA 110 also allows EMR-generated alerts to be formatted and sent into the patient communication thread (in a configurable manner either by a "setting" option or by voice command, such as telling it, e.g., "don't show me this again"). The EMR VHA 110 may also serve as a drug safety alerting system (including allergies, drug-to-drug relations, etc.) and may be thus connected to a relevant medical knowledgebase.

Guideline VHA 112 is configured to retrieve relevant care guidelines from an external guideline service 124. Guideline VHA 112 may be prompted, via communication occurring on communication channel, to retrieve care guidelines. For example, a care provider may explicitly request care guidelines for a given condition, such as sepsis, on the communication thread and guideline VHA 112 may query external guideline service 124 in response to the explicit request. In other examples, guideline VHA 112 may determine implicitly that care guidelines for a given patient condition are being requested and/or may be helpful. For example, guideline VHA 112 may parse communication on the communication thread 104 (e.g., between one or more care providers and/or a suitable VHA) to determine that guidelines are being requested (e.g., rather than receiving an explicit request for the guidelines, guideline VHA 112 may determine that two care providers are discussing guidelines and may retrieve the guidelines without being requested to do so). In a further example, guideline VHA 112 may determine, from patient vital signs (e.g., output by the one or more monitoring devices 120), digital twin 108, and/or other sources that a patient may be undergoing a given condition (e.g., high heart rate) and may automatically obtain guidelines for treating the condition.

External guideline service 124 may be a remote service accessed via a network, or external guideline service 124 may be a local service executed on a computing device of the hospital. The care guidelines obtained from external guideline service 124 may be preconfigured by protocols and guidelines that are specific to the medical facility that the collaborative space server system 102 services. Further, external guideline service 124 may include differential diagnoses trees that guideline VHA 112 may access to determine potential diagnoses based on a patient condition or state.

For example, with regards to the patient's state and medical history as search terms, e.g., if a diabetic patient has a high sequential organ failure assessment (SOFA) score and high glucose levels, specific guidelines will be queried without additional query terms, or alternatively the external guideline service may be queried by specifying specific guidelines. In other words, the guideline VHA may enter specific search terms to the guideline service based on patient state and symptoms (e.g., diabetes, SOFA score of five, glucose level of 190 mg/dL) to obtain one or more potential diagnoses and/or guidelines, or the guideline VHA may specifically ask for guidelines for a given condition (e.g., sepsis). The guideline VHA may also serve as a source for generating reminders for treatments that are part of a care protocol or to keep track of what decision-driving tests have been completed and what are still needed to complete the protocol. A change in patient status may be a trigger for automatic notification of relevant guidelines. The guideline VHA may also be used to plan a trajectory for the patient, of both disease progression and a care path. A patient trajectory may be determined based on the combined trajectories of vital signs, laboratory test results, or other data for that specific patient. In defining a patient trajectory, the guideline VHA may assist care providers to adjust care pathways or to stay the course and give early warning if the patient deviates from the planned trajectory.

Predictive VHA 114 is configured to retrieve predictions of future patient states from an external prediction service 126. Predictive VHA 114 may detect and issue alerts on relevant changes in the patient's state (e.g., small but worrying changes in vital signs, changes in qSOFA score). Predictive VHA 114 may also predict future events (e.g., a prediction of sepsis being developed in the coming four hours) by connecting to external prediction service 126. Predictive VHA 114 may query external prediction service 126 with search terms indicating current and/or past patient state (e.g., blood pressure trend, glucose level trend, etc.). If prediction service 126 outputs a possible future condition, the predictive VHA 114 may send an alert into the communication thread, as text, and may provide supplemental information regarding the alert. The predictive VHA 114 may also track the response of human care providers as reflected in the communication channel or in the EMR orders registry. The predictive VHA 114 may obtain patient data from the EMR and different online monitoring devices 120 (ECG, cameras, etc.) as represented in the digital twin.

Listening VHA 116 is configured to monitor communication on the communication thread 104 as well as actual human voice communication to obtain/infer various information related to the patient. In doing so, listening VHA 116 serves as a monitor, by listening to the events in the patient's surroundings including medical staff conversations and patient input (from moaning to speech). The monitored conversations/inputs may be used to record the patient's status (for EMR/digital twin) or to infer clinician reasoning (e.g., the listening VHA may catch an order to prescribe a certain antibiotic by a doctor, and understand an infection is suspected). The listening VHA 116 may receive output from one or more microphones positioned in proximity to the patient, for example, in order to monitor the conversations and inputs.

Monitoring VHA 117 is configured to receive output from the monitoring devices 120 and may track a patient condition or state based on the received output. In some examples, monitoring VHA 117 may present the received data via the communication thread and/or dashboard. For example, a care provider may send a request to the monitoring VHA 117, through the communication channel, for a particular piece of patient monitoring data, such as current heart rate. The monitoring VHA 117 may receive the request and determine, from the natural language of the request, that the patient medical data has been requested. The monitoring VHA 117 may obtain the patient medical data from the relevant monitoring device of the monitoring devices 120. The monitoring VHA 117 may then send the medical data to the care provider in the form of a message on the communication thread 104. In some examples, monitoring VHA 117 may be configured to save the medical data at the digital twin 108. Further, medical data received by monitoring VHA 117 may be displayed via the dashboard. In some examples, monitoring VHA 117 may obtain patient medical data only in response to a request from a care provider. In other examples, additionally or alternatively, monitoring VHA 117 may obtain medical data from the monitoring devices 120 independently of care giver request, and may output requested medical data when a care giver requests the data and/or when the received medical data is detected (by the VHA) as being abnormal, having changed, or otherwise indicative of an urgent patient state. In some examples, monitoring VHA 117 may be configured to provide received medical data to predictive VHA 114 and/or guideline VHA 112 in order to predict a future patient state based on current patient medical data and/or retrieve relevant care guidelines based on current patient medical data.

The VHAs may be configured to receive messages from human care providers and utilize natural language processing to determine what information is being conveyed in the messages. For example, the VHAs may utilize natural language processing to determine if a message received on the communication channel includes a request for patient medical information, and if so, determine what medical information is being requested. The VHAs may also be configured to process medical information of the patient (e.g., vital signs, medical history, current symptoms) received from the patient EMR, the monitoring devices, the care providers, and/or other sources and determine which parameters of the medical information may be used (e.g., entered into the guideline or prediction service) to determine a patient state (such as determine the likelihood the patient is experiencing a certain condition, such as sepsis). The VHAs may execute deep learning models (e.g., machine learning or other deep learning models such as neural networking) that are trained to understand medical terminology. Further, the deep learning models may be configured to learn updates or modifications to the models in an ongoing manner in a patient and/or care provider specific manner. For example, a predictive VHA may execute a deep learning model that is trained to determine that low blood pressure may be a symptom of relevance that should be entered into a prediction service or diagnosis tree, but then may be trained for a specific patient that low blood pressure for that patient is benign and may have less relevance.

The models may be trained in a suitable manner. In a first example, the models may be rule-based assistants that are configured with a set of answers for predetermined, likely questions. When a VHA receives a question, the VHA may be configured to output an answer from the set of answers. In a second example, the models may include directed acyclic graphs (DAG) of states, each of which include rules for how to react and how to proceed to various questions. However, such VHAs may only be configured to respond when there is a clear indication of the user intent (e.g., the user presses on a button "obtain heart rate") and entities (answer to "please provide the patient's date of birth" with a date).

Thus, the VHAs described herein may include artificial intelligence and be adapted to handle natural language which is a way to take human input and map it to intent and entities. The VHAs may be adapted to hold a state and map the state with (intent, entities) to an actionable API. The mapping may be performed by teaching machine learning models by providing the models with examples of such mappings. If a VHA is autonomous, the VHA may include a prediction or other mechanism that may trigger the VHA to initiate communication. The VHAs may also be configured to vary their reactions to make the VHAs more human like (this may also be performed by providing examples to a machine learning training algorithm).

Further, the training mechanism utilized may be specific for different VHAs. For example, the listening VHA (and the natural language processing engines of the other VHAs) may execute deep networks trained for natural language with medical language. This may be combined with taxonomies from the medical domain. The EMR VHA and the guideline VHA may receive the output (intent and entities) from the listening VHA and/or the respective natural language processing engine and map the output to queries. The VHAs may be trained by having examples of the best results of existing queries. The predictive VHA may be trained on its own clinical task. For example, if the predictive VHA is to predict if a patient will survive early release from an intensive care unit, then the predictive VHA may be trained on data of patients that were in the ICU and were released at different stages.

Additional VHAs may be included on the server system, such as VHAs specific to a patient state. Such an example may include a sepsis VHA that may only be joined to a patient communication channel when that patient is undergoing or at risk of developing sepsis. The sepsis VHA may be trained to specifically predict sepsis, obtain treatment guidelines for sepsis, suggest optimal lab tests to diagnose sepsis and/or monitor sepsis progression, and/or suggest treatment options for sepsis. Other VHAs may include a patient comfort VHA (e.g., a VHA configured to detect or predict patient pain, discomfort, hunger, or other symptoms not necessarily indicative of a particular medical condition but which care providers may want to be notified of to improve patient comfort), a communication VHA (e.g., that parses communication from care givers and facilitates sharing of information among the VHAs), and/or other VHAs. Further, various configurations of VHAs not disclosed above are within the scope of this disclosure, such as related VHAs being grouped into a single VHA (e.g., the monitoring and EMR VHAs being combined as one medical data VHR). For example, a single VHA may be trained for all of the above-described VHA possible skills.

A global view of multiple or all patient communication thread-dashboard pairs may be provided via to one or more of the care provider devices and the hospital operational systems 118. For example, the choice of the specific thread/dashboard pair to access may be controlled by an access application executing on collaborative space server system 102 that allows to a user to view all the relevant patients (for example, communication thread-dashboard pairs for all the patients being treated/monitored in a nurses station may be accessed on a workstation at the nurses station, or communication thread-dashboard pairs for all the patients being treated/monitored by a given care provider may accessed by that care provider on his or her mobile device). In some examples, alerts and important events within all the relevant communication channels will be signified in the global view. The choice to go into a specific communication channel may be made by a user picking the patient in the global view (or by an explicit voice command), but may be also be automated using automatic mechanisms which may detect the position of the care provider in respect to a patient (such as via BLUETOOTH® when entering a patient's proximity or based the context of a detected discussion).

The access application may allow export of only specific widgets (such as the blood pressure graph of a patient) of a communication thread and/or dashboard, or may allow more compound parts (such as a patient dashboard or a portion of the thread) to selected external applications and/or devices. For example, as explained above, devices located off-site of the medical facility may only be allowed access to some of the patient medical data, and the access application may control which patient medical data is viewable outside of the medical facility.

A management application executed on hospital operational systems 118 and/or collaborative space server system 102 may allow an administrator to update the care team that has access to a patient's communications channel, as described above. The management application may include an interface for configuring hospital specific protocols and care guidelines. The management application may also aggregate information from the communication channels to be used to predict needs for hospital operations, presenting forecasts for capital, disposable, and human assets based on aggregate acuity or disease statistics. Moreover, analytics of the information on the communication channel may be employed to improve the system and its predictors.

Collaborative space server system 102 includes a communication module 128, memory 130, and processor(s) 132 to store and execute the communication channel-dashboard pairs, digital twins, and VHAs, as well as send and receive communications, graphical user interfaces, medical data, and other information.

Communication module 128 facilitates transmission of electronic data within and/or among one or more systems. Communication via communication module 128 can be implemented using one or more protocols. In some examples, communication via communication module 128 occurs according to one or more standards (e.g., Digital Imaging and Communications in Medicine (DICOM), Health Level Seven (HL7), ANSI X12N, etc.). Communication module 128 can be a wired interface (e.g., a data bus, a Universal Serial Bus (USB) connection, etc.) and/or a wireless interface (e.g., radio frequency, infrared, near field communication (NFC), etc.). For example, communication module 128 may communicate via wired local area network (LAN), wireless LAN, wide area network (WAN), etc. using any past, present, or future communication protocol (e.g., BLUETOOTH®, USB 2.0, USB 3.0, etc.).

Memory 130 one or more data storage structures, such as optical memory devices, magnetic memory devices, or solid-state memory devices, for storing programs and routines executed by processor(s) 132 to carry out various functionalities disclosed herein. Memory 130 may include any desired type of volatile and/or non-volatile memory such as, for example, static random access memory (SRAM), dynamic random access memory (DRAM), flash memory, read-only memory (ROM), etc. Processor(s) 132 may be any suitable processor, processing unit, or microprocessor, for example. Processor(s) 132 may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, server system 102 is shown in FIG. 1 as constituting a single entity, but it is to be understood that server system 102 may be distributed across multiple devices, such as across multiple servers.

While not specifically shown in FIG. 1, additional devices described herein (care provider device 134, care provider device 136, and care provider device 138, hospital operational systems 118, monitoring devices 120, EMR database 122, external guideline service 124, external prediction service 126) may likewise include user input devices, memory, processors, and communication modules/interfaces similar to communication module 128, memory 130, and processor(s) 132 described above, and thus the description of communication module 128, memory 130, and processor(s) 132 likewise applies to the other devices described herein. As an example, the care provider devices (e.g., care provider device 134) may store user interface templates in memory that include placeholders for relevant information stored on server system 102. For example, care provider device 134 may store a user interface template for a patient dashboard that a user of care provider device 134 may configure with placeholders for desired patient information. When the dashboard is displayed on the care provider device, the relevant patient information may be retrieved from server system 102 and inserted in the placeholders. The patient information may include current patient vital signs, VHA alerts, desired patient state trends, or other information, as explained in more detail below. The user input devices may include keyboards, mice, touch screens, microphones, or other suitable devices.

FIG. 2 shows an example communication thread 200 of a patient-specific communication channel, and as such may be a non-limiting example of communication thread 104. Communication thread 200 may be displayed on a display device 202. Display device 202 may include a screen on which the communication thread is displayed and may be coupled to and/or included as a part of a computing device, such as care provider device 134. Communication thread 200 may be displayed in response to a user request to display the communication thread. For example, the user (e.g., a care provider) may access a collaborative system interface that includes a global view of all communication threads and dashboards the user is authenticated to participate in (which may include all patients at the medical facility the care provider is attending to) and may select a desired communication thread to view. An example collaborative system interface 500 is shown in FIG. 5. Collaborative system interface 500 may be displayed on display device 202 or other suitable device and may include all patients admitted to a specific unit or ward of a medical facility. As shown, collaborative system interface 500 includes identifying information specifying the medical facility ("acute care center") and relevant unit ("ward 1") of the medical facility, and further includes links to patient-specific communication threads and dashboards for the patients in that unit of that medical facility. However, in other examples, the patients shown via collaborative system interface 500 may specific to a certain care provider.

Collaborative system interface 500 may include a notification section whereby the user viewing collaborative system interface 500 may be notified of urgent patient conditions, active communication channel discussions, lab test results, and other information. For example, collaborative system interface 500 includes a notification section that shows that one patient requires attention (e.g., due to deteriorating vital signs) while two new discussions are available.

Collaborative system interface 500 further includes links to patient communication thread-dashboard pairs. For example, FIG. 5 shows links to communication thread-dashboard pairs for patient ID 0123, patient ID 1111, patient ID 1234, and patient ID 1235. As explained above, each patient may be assigned an identifier that may be used to identify the patient on the communication thread and dashboard. In other examples, other mechanisms for identifying the patient may be used, such as location (e.g., bed 2 in room 4) and/or actual patient name. Additional patient links may be viewed by scrolling the interface. Each patient link may include notifications where relevant. For example, the link for patient ID 1111 includes a notification that three new messages are available to be viewed on the communication channel for that patient. The link for patient ID 1234 includes a notification that action is needed (e.g., due to high blood pressure or other significant vital sign being detected) as well as a notification that one new message is available on the communication channel for that patient. In some examples, when a lab test result for a patient is available, the link for that patient may include a notification of an available lab test result, such as the notification displayed in the link for patient ID 1235. In examples, care providers may be notified of available lab test results through the communication channel for the patient, and thus the notification may include a notification that a new message is available.

Selection of a patient link may launch the communication thread or dashboard for that patient. For example, selection of the link for patient ID 1234 may launch the communication thread 200 for patient ID 1234, shown FIG. 2 and explained in more detail below.

Returning to FIG. 2, communication thread 200 may include an identification header 204 that identifies the patient being discussed/monitored via the communication thread. In the illustrated example, communication thread 200 is specific to patient ID 1234. In the illustrated portion of communication thread 200, communication is occurring between a care provider (e.g., Dr. Smith) and a virtual healthcare assistant that, in the illustrated example, has a human persona and as such includes a human name (Alan). Communication thread 200 is being viewed by Dr. Smith, although any authenticated/approved user (e.g., a member of the care team assigned to that patient) may view communication thread 200. As shown by the first message from the top, Dr. Smith is requesting medical information relating to the patient from the VHA by asking, in natural language, for a heart rate graph ("Could I get the HR graph please"). In response, the VHA sends an image of the patient's heart rate graph, which may be obtained or assembled from the patient's EMR data, for example. The image of the heart rate graph is viewable in the communication thread and may also be selected via suitable user input to view in a different form, such as via the patient dashboard.

At a later time (e.g., 4:00 PM), the VHA outputs an alert/notification in the communication thread indicating a change in patient status, herein a deterioration in vitals. The alert is accompanied by a suggested course of action that a care provider may take, including checking respiratory rate and mental state. The VHA issues another alert at 5:00 PM indicating that sepsis is suspected based on a quick SOFA score (qSOFA), owing to low systolic blood pressure and a low Glasgow coma scale. The alerts issued by the VHA may include links to the patient dashboard, for example, allowing a user to select a link to launch the dashboard and view the medical data relating to the alerts. For example, the alert "systolic BP is less than 100 mmHg" is shown in underline, indicating a link to additional information is available. A user may select the link via a suitable input, such as via a mouse click, touch input, or voice command. In some examples, selecting a link with a first selection (e.g., a double click) may launch the patient dashboard (as shown in FIG. 3). Selecting a link with a second selection (e.g., a single click or a hover) may launch a preview where only the patient's blood pressure graph is shown.

In response to the alert regarding the potential sepsis, Dr. Smith asks for guidelines at 5:01 PM. Because the VHA had immediately previously issued the alert regarding the possible sepsis due to the qSOFA score, the VHA may assume that the guidelines being requested by Dr. Smith include guidelines for sepsis based on a qSOFA score. In response, the VHA retrieves guidelines from an external guideline service relating to qSOFA scores and outputs the guidelines into the communication thread. As shown, only a portion of the guidelines are displayed in the communication thread. By selecting the link (the underlined "qSofa guidelines"), the user may be taken to a different interface where the full guidelines are displayed, or the full guidelines may be displayed over the top of the still-displayed communication thread.

While not shown in FIG. 2, communication thread 200 may include a search box/functionality where a user may search for past messages on the communication thread. For example, a user may enter a command (by voice or text) requesting that all messages related to the patient's heart rate be displayed. Also displayed on display device 202 is a communication thread button 206 and a dashboard button 208. In FIG. 2, the user is viewing the communication thread 200 occurring on the communication channel. Hence, the communication thread button 206 is highlighted. To switch to the dashboard for patient ID 1234, the user may select the dashboard button 208. Additionally or alternatively, the user may request to view a vital signs interface by selecting a link within the identification header 204 (e.g., by selecting "vitals"). The vital signs interface, which is discussed in more detail below with respect to FIG. 6, may serve as an additional or alternative dashboard, wherein additional medical information of the patient may be displayed. The user may request to view additional interfaces via the identification header 204, such as a labs interface, where lab results may be displayed, a meds interface, where medicine dosage, timing, and other information may be displayed, and an orders interface, where testing orders (such as diagnostic imaging tests, lab tests, or other tests) may be displayed.

As explained above, FIG. 2 shows communication between a care provider and a virtual healthcare assistant ("Alan"), where Alan provides all the information requested by the care provider as well as provides alerts/notifications. In this way, Alan is performing the functions described above with respect to FIG. 1 ascribed to the predictive VHA, EMR VHA, and guidelines VHA. It is to be understood that in some examples, each of the different VHAs may interact with the communication thread individually.

The communication thread 200 shown in FIG. 2 may be an example of a public communication thread, and as such all messages sent and received on the communication thread 200 may be viewed by all members of the patient's care team. It is to be understood that when a user requests to communicate over a private communication thread, the same interactions between the user/care provider and the one or more VHAs that were described above may still apply. That is, the private communication thread may be similar to the public communication thread in that the care giver on the private communication thread may enter requests to the one or more VHAs using natural language, and the one or more VHAs may respond by retrieving information specified by the requests and formatting the information into natural language messages, images, graphs, etc., and outputting the formatted information into the private communication thread. The private communication thread may differ from the public communication thread in that the private communication thread may only include communication between a single care provider and the one or more VHAs.

FIG. 3 shows an example dashboard 300 that may be displayed on display device 202 or other suitable device. Dashboard 300 may be displayed in response to a user input to the communication thread 200, for example by selecting a link within medical information displayed in communication thread, as explained above, or in response to selection of the dashboard button 208. However, dashboard 300 may be displayed in response to other inputs, such as in response to a user input selecting the dashboard from the collaborative system interface of FIG. 5 that includes a global view of multiple communication threads and dashboards. Additionally, FIG. 3 shows a side bar 302 displayed along with dashboard 300 showing patient dashboards for the patients Dr. Smith is currently attending. User input to the side bar may launch a different dashboard, for example Dr. Smith may select to view each of the currently available dashboards to quickly assess the status of each patient.

Dashboard 300 may be configured to display patient medical information based on the current patient state and user-configured settings. For example, a dashboard for a patient that is being treated at the medical facility for pneumonia may be configured to display different medical information than a dashboard for a patient that is being treated at the medical facility for a stroke. In some examples, when a patient is admitted at the medical facility, a dashboard may be generated automatically for the patient based on the reason of admittance (e.g., pneumonia), thereby including the most relevant patient medical information for the patient's condition, such as blood oxygen level and respiration rate. A user may also configure which medical data to view via the dashboard, for example a doctor attending to the patient may choose to view heart rate rather than respiration rate.

The medical information that is displayed on the dashboard may be obtained from one or more monitoring devices currently monitoring the patient, such that the medical information is displayed on the dashboard in a real-time (or near real-time) manner. Additionally or alternatively, the medical information that is displayed on the dashboard may be obtained from the patient's EMR, the digital twin associated with the patient, and/or the communication thread. As explained above, one or more VHAs may obtain patient medical information from the patient's EMR, the monitoring devices, guideline services, or other sources and include the obtained medical information as a message in a communication thread on the communication channel. To view the medical information in greater detail, the user may select the medical information from the communication thread, where the medical information may then be displayed in the dashboard.

Additional information may also be displayed via the dashboard, such as patient information (location, demographics, medical history), care provider information (such as which doctors, nurses, and/or other care providers are attending to the patient), and a timeline of selected or relevant messages from the communication thread. For example, the most recent alerts may be displayed as a timeline on the dashboard.

Referring to dashboard 300 as an example, patient information 304 is displayed at the top of the dashboard, including patient identification and location. Care provider information 306 is also displayed in dashboard 300, including current care providers for the patient. Additionally, a user interface control button 308 is shown that, when selected, may allow the care provider viewing dashboard 300 to view and interact with the communication thread.

Dashboard 300 further includes real-time medical information indicators 310. As shown, the indicators 310 include a SOFA score and blood glucose level, depicted as gauge charts with respective needles that move to indicate current SOFA score and blood glucose relative to a range of possible SOFA scores and blood glucose levels. While not shown in FIG. 3, the gauge charts may include color coding for quick determination of normal, intermediate, and high scores/levels, for example. The gauge charts shown are exemplary in nature and patient medical information may be shown in other forms.

Dashboard further includes medical history trends, including a first graph 312 depicting mean arterial blood pressure trend (e.g., blood pressure as a function of time) and a second graph 314 depicting blood glucose trend (e.g., blood pressure as a function of time). The medical history trends shown in FIG. 3 may be displayed on the dashboard in response to a request from a user (e.g., in response to a care provider selecting a link to patient medical history from a communication thread), due to a preconfigured dashboard setting, or other suitable trigger. For example, as shown in FIG. 2, the VHA issued an alert at 5:00 PM that included reference to patient blood pressure in the form of a link. When the link is selected (e.g., via cursor 204), the dashboard 300 may be displayed showing the first graph 312 of the patient's blood pressure trend.

Dashboard 300 further includes a recent lab test results section 316, where the results from recent lab tests may be displayed. For example, the user may have selected a link to available procalcitonin (PCT) test results displayed as part of a communication thread, which may result in display of dashboard 300. Via the recent lab test results section 316, the user (care provider) may be notified that the PCT test for that patient is relatively high and thus sepsis is confirmed or suspected.

As explained earlier, one or more of the virtual healthcare assistants may be configured to monitor patient vital signs, via the output from the monitoring devices, the information stored in the digital twin, or other source. If a vital sign (or other health parameter) meets a predetermined condition, the one or more virtual healthcare assistants may be configured to output an alert to notify the one or more care providers attending the patient that patient follow-up may be needed. The alerts may be included in the communication thread, as discussed above. Additionally or alternatively, the alerts may be displayed on the dashboard. As shown, first graph 312 includes two alerts, each alert issued when mean arterial blood pressure dropped below a threshold, such as 80 mmHg, or trended in an unexpected way, such as five consecutively decreasing values which may or may not be below the 80 mmHg threshold. Selection of an alert may trigger display of a portion of the communication thread occurring on the communication channel where the alert was referenced.

Thus, as shown in FIG. 4, in response to user input selecting the second alert displayed on the dashboard 300 (e.g., the "alert 2" box) via cursor 204, a portion 402 of the communication thread 200 shown in FIG. 2 is displayed over dashboard 300. The portion 402 displayed may include only the portion of the communication thread that references the medical information that triggered the alert, and may also include additional messages around the message referencing the alert, in order to place the alert in context. In this way, a user may be able to quickly determine what else may have occurred around the time the alert was issued, determine if attending care providers administered treatment, or determine other relevant information. The portion 402 may not include the most recent messages in the communication thread, in some examples. Further, a user may not have access to the full communication thread when viewing the portion, and may not be able to interact (e.g., send messages) with the communication channel. Thus, a different selection on the dashboard may enable a user to view the full communication thread.

Additionally or alternatively, when viewing the portion of the communication thread, the user may scroll to view other portions of the communication thread or may enter another input to the portion of the communication thread to enable viewing of the full version of the communication thread. Alternatively, instead of showing a snippet from the communication channel, the full version of the communication thread may be displayed, with the focus point being the point in the communication channel that references the alert (which may enable the user to look before and after that point of the thread if desired). In another example, only the snippet of the communication thread may be displayed and if the snippet is selected, the full version of the communication thread may be displayed. In this way, either automatically or upon a further user input, the user may be able to interact with the communication thread (e.g., send a message via the communication thread).

Thus, the collaborative healthcare system shown in FIG. 1 may generate communication thread-dashboard pairs for each patient associated with the collaborative healthcare system. The collaborative healthcare system may include one or more computing devices, such as the care provider device 134. The computing device may include a display screen, and the computing device may be configured to display on the screen a dashboard. The dashboard may include patient medical information, such as diagnostic lab test information (e.g., lab test results, pending lab tests that have been ordered but not yet fulfilled, status updates for pending lab tests, and so forth). The computing device may additionally be configured to display on the screen an alert related to the patient medical information. For example, as shown in FIG. 3, dashboard 300 may be displayed on a screen of a computing device (e.g., display device 202, which may be a screen of a computing device such as care provider device 134). Dashboard 300 may display patient medical information, such as the graph of the blood pressure trend of the patient (e.g., first graph 312) and recent lab results. The displayed medical information may include an alert, such as alert 2 shown on first graph 312.

The alert may be selectable to launch a communication thread between a care provider and a virtual healthcare assistant. For example, as shown in FIG. 4, selection of alert 2 launches a communication thread between a care provider (Dr. Smith) and a virtual healthcare assistant (Alan). The selection of the alert enables a portion of the communication thread that references the displayed patient medical information to be seen within the communication thread. For example, FIG. 4 shows that in response to selection of alert 2, a portion 402 of the communication thread 202 (shown in FIG. 2) is displayed. The portion 402 includes reference to patient blood pressure, which is also displayed on the patient dashboard. Further, the alert may be displayed on the dashboard (at least initially) while the communication thread is in an un-launched state. For example, the alert may be displayed on dashboard 300 without display of the communication thread, e.g., while the communication thread is un-launched. In some examples, the full communication thread may be displayed rather than just a portion, with the full communication thread focused at the portion that references the patient blood pressure. According to some embodiments, the communication thread and the dashboard may both be displayed simultaneously on the display device. When a communication thread is launched from a dashboard (e.g., in response to user selection of an alert), the launched communication thread may be a public communication thread. The public communication thread may be the default communication thread that is launched when a communication thread is requested, and the private communication thread (e.g., between a particular care provider and the one or more VHAs) may only be launched in response to an explicit request to launch the private communication thread, as will be explained in more detail below.

In this way, the computing device provides a specific manner of displaying a limited set of information (e.g., the portion of the communication thread that specifically references medical information displayed on the dashboard) to the user, rather than using conventional user interface methods to display a generic index/list on a computer that may require the user to step through multiple menus and/or lists of communications and alerts to find the relevant portion of communication regarding the medical information. The dashboard interface-communication thread link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed dashboard interface-communication thread link may improve the efficiency of using the computing device by bringing together the portion of the communication thread most relevant to the user (as it relates to the displayed medical information) and the dashboard actually displaying the medical information, allowing the user to view the most relevant information on the communication thread without actually opening up the communication thread. The speed of a user's navigation through various views and windows may be improved because the disclosed link between the dashboard and the communication thread saves the user from navigating to the communication thread from the dashboard, opening the communication thread up, and then navigating within the communication thread to enable the portion of interest to be seen or a function of interest to be activated.

Thus, the collaborative healthcare system shown in FIG. 1 may generate communication thread-dashboard pairs for each patient associated with the collaborative healthcare system. The collaborative healthcare system may include one or more computing devices, such as the care provider device 134. The computing device may include a display screen, and the computing device may be configured to display on the screen a communication thread. The computing device may additionally be configured to display on the screen a dashboard that can be reached directly from the communication thread. For example, as shown in FIG. 2, the communication thread may include a link that when selected launches a dashboard, such as the dashboard 300 shown in FIG. 3.

The communication thread displays communication between a care provider and a virtual healthcare assistant, and the communication thread includes medical information of a patient. At least a portion of the displayed medical information is selectable to launch the dashboard and enable the selected medical information to be seen within the dashboard. For example, referring to FIG. 2, the communication thread includes a link referencing patient medical information (herein, patient vital signs), and selection of the link launches some or all of the dashboard. The dashboard includes display of the patient medical information included in the link (e.g., the vital signs). In an example, selection of the link may launch a full version of the dashboard, as shown in FIG. 3. In another example, selection of the link may launch only a portion of the dashboard. The communication thread may be displayed while the dashboard is in an un-launched state, at least initially. For example, FIG. 2 shows the communication thread being displayed without display of the dashboard, and thus the dashboard may be unlaunched until the link the communication thread is selected.

In this way, the computing device provides a specific manner of displaying a limited set of information (e.g., the dashboard that specifically includes medical information referenced in the communication thread) to the user, rather than using conventional user interface methods to display a generic index/list on a computer that may require the user to step through multiple menus and/or lists of communications and alerts to find the relevant medical information. The communication thread-dashboard interface link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed communication thread-dashboard interface link may improve the efficiency of using the computing device by bringing together the medical information most relevant to the user (via the dashboard) and the communication thread referencing the medical information, allowing the user to view the most relevant medical information discussed on the communication thread without actually accessing an electronic medical record or separate interface where patient monitoring data may be displayed. The speed of a user's navigation through various views and windows may be improved because the disclosed link between the communication thread and dashboard saves the user from navigating to an electronic medical record database, opening the database up, and then navigating within the database to enable the medical information of interest to be seen or a function of interest to be activated.

As mentioned previously, an identification header may be displayed with the communication thread and may include patient identification information and user interface control buttons via which a user may enter input selecting to view a different interface related to that patient. As an example, the identification header may include a vitals button, and user selection of the vitals button (e.g., via a touch input) may cause a vital signs interface for that patient to be displayed. FIG. 6 shows an example of a vital signs interface 600 that may be displayed on a display device 602. Display device 602 may include a screen on which the vital signs interface is displayed and may be coupled to and/or included as a part of a computing device, such as care provider device 134 shown in FIG. 1.

Vital signs interface 600 includes an identification header 604, similar to the identification header described above with respect to FIG. 2. Vital signs interface 600 further includes a plurality of patient medical parameters. The plurality of patient medical parameters may include a plurality of vital signs measured by one or more patient monitoring devices, which may be stored in the patient's EMR and/or as part of the patient's digital twin. The plurality of vital signs may include temperature, heart rate, blood pressure, mean arterial pressure, respiratory rate, O2 saturation, and oxygen level, as shown, and/or may include additional or alternative vital signs. The plurality of patient medical parameters may further include assessed patient states, which may be ascertained by one or more care providers and entered into the patient's EMR. The assessed patient states may include pain (as shown), alertness level, cognition, appearance, etc.

For each medical parameter displayed on the vital signs interface 600, a name of the medical parameter may be displayed along with the most recently-recorded value for that parameter and the time/date at which the value was recorded. For example, the first vital sign displayed from the top of the vital signs interface includes temperature with a value of 36.9° C. recorded at 14:20. For some, or all, of the patient medical parameters displayed on the vital signs interface, user selection of that medical parameter may result in additional information being displayed, such as a trend graph for that parameter that may include some or all of the measured values for that parameter over a given duration.

For example, as shown, a user has selected the blood pressure parameter, e.g., by entering a touch input to the blood pressure parameter displayed on the interface. As a result, a blood pressure trend graph 606 is displayed (e.g., the blood pressure section may expand downward to accommodate the graph, shifting all other parameters below it downward). The blood pressure trend graph 606 includes six blood pressure values measured in the past 24 hours and plotted as a function of time (as each blood pressure measurement includes systolic and diastolic pressure, two curves are shown, one for systolic and one for diastolic). User deselection of the blood pressure parameter (e.g., by selecting it again) may cause the blood pressure region to collapse back to its original size and displayed information, resulting in the blood pressure trend graph not being displayed. Similar trend graphs may displayed upon user selection of any of the displayed medical parameters.

The medical parameters that are displayed as part of the vital signs interface may be selected in a suitable manner. In one example, the user may customize which parameters are displayed on the vital signs interface, whether globally for all patients that the user interacts with or individually by patient. In other examples, an administrator (e.g., of the hospital) may determine which parameters are displayed. In still further examples, additionally or alternatively, the medical parameters included in a particular patient's vital signs interface may be based at least in part on the patient's diagnosed condition(s) and/or reason for admittance to the medical unit. For example, a vital signs interface specific to a patient that is diagnosed with pneumonia may have at least some different medical parameters than a vital signs interface specific to a patient undergoing a C-section.

The vital signs interface illustrated in FIG. 6 may be displayable in addition to the patient dashboard illustrated in FIGS. 3 and 4. In this way, both the dashboard of FIGS. 3 and 4 and the vital signs interface of FIG. 6 may be available to care givers as different interfaces for viewing select patient medical information. In other examples, the vital signs interface and the dashboard illustrated in FIGS. 3 and 4 may be alternative embodiments, e.g., the vital signs interface may be one example of how a dashboard may be configured and the dashboard of FIGS. 3 and 4 may be a different example of how a dashboard may be configured. In still other examples, the vital signs interface may be a "mobile interface" and the dashboard (such as the dashboard of FIGS. 3 and 4) may be a "standard interface," such that the dashboard may be viewed when the care provider device is a desktop computer, laptop, large format monitor, etc., while the vitals interface may be displayed when the care provider device is a mobile device, such as a smartphone or tablet, or otherwise includes limited display area.

Figure 7:
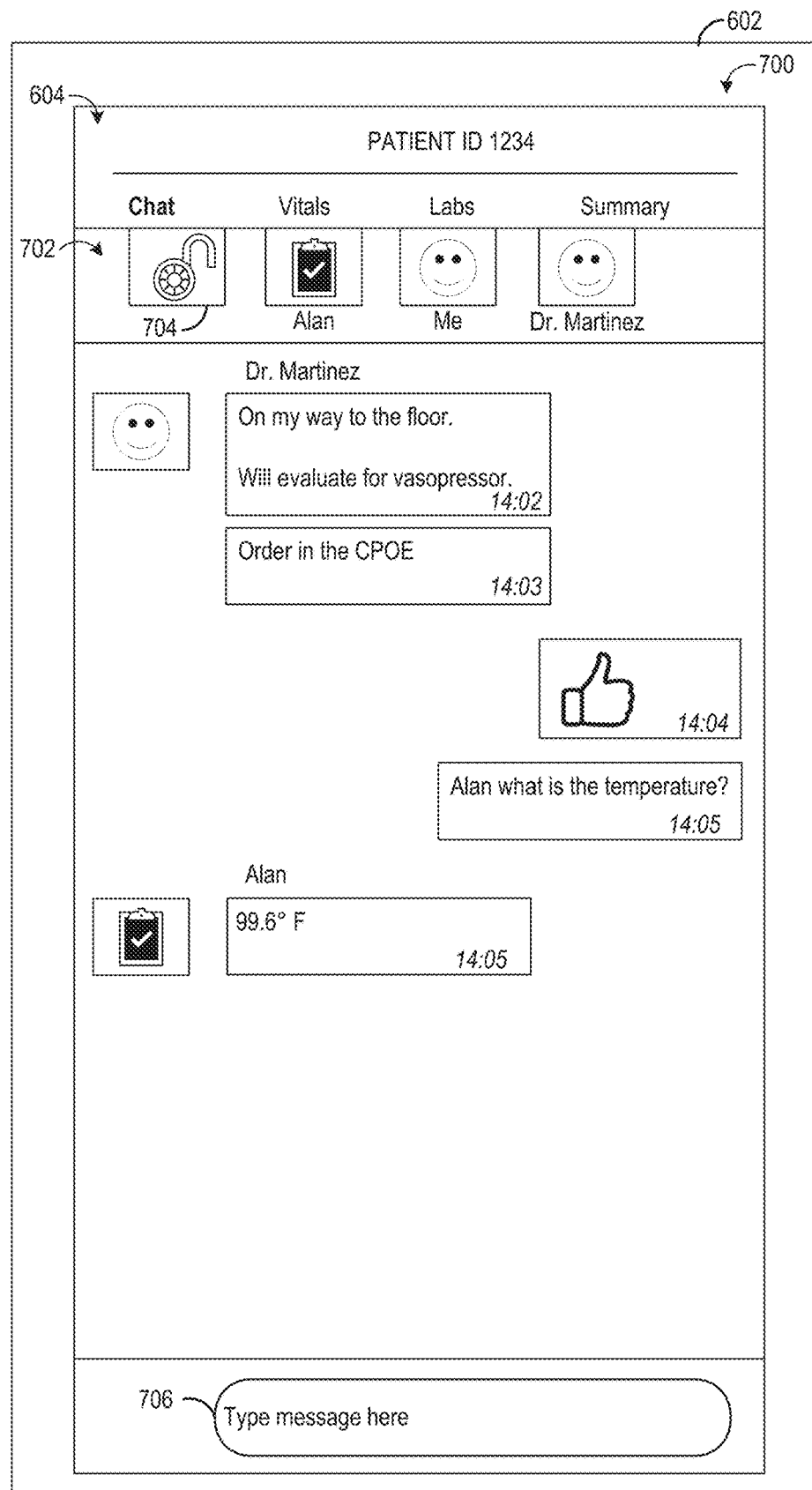
FIGS. 7 and 11 show an example display device displaying an example public communication thread occurring on a communication channel of the collaborative healthcare system.

As mentioned previously, identification header 604 may include identifying information for the patient to which the displayed interface is directed to. Identification header 604 may further include a plurality of tabs/links that a user may select to launch different pages of information specific to the patient, including a chat tab, vitals tab, labs tab, and summary tab, although other tabs are possible without departing from the scope of this disclosure. For example, by selecting the chat tab, a public communication thread specific to the patient (e.g., patient 1234) may be launched, as shown in FIG. 7. FIG. 7 illustrates an example public communication interface 700 that is displayed on display device 602. A public communication thread specific to a patient is displayed via the public communication interface 700. Communication on public communication interface 700 is occurring between a virtual healthcare assistant, herein referred to as Alan, and two care providers, Dr. Smith and Dr. Martinez. Public communication interface 700 includes a group chat identifier 702 wherein each VHA and/or care provider joined to that patient's public communication thread is shown. Thus, icons (which may be referred to as chat icons) are displayed for Alan, Dr. Smith (shown as "me" as the public communication interface 700 is being displayed on a device belonging to Dr. Smith), and Dr. Martinez. Further, group chat identifier 702 includes a public/private icon 704 that indicates the public communication thread is being displayed. In the public communication interface 700, the public/private icon 704 shows an unlocked padlock to indicate that the communication thread is public.

The communication thread displayed via public communication interface 700 and shown in FIG. 7 includes communication between Dr. Martinez, Dr. Smith, and Alan. As shown, Dr. Martinez notifies the care team (e.g., Dr. Smith) that she is on her way to the floor to evaluate the patient for vasopressor and also notifies the care team that an order (e.g., for a vasopressor) has been entered into the computerized physician order entry (CPOE). Dr. Smith acknowledges the messages from Dr. Martinez and then sends a message onto the public communication thread asking the VHA (Alan) for the patient's temperature. For example, Dr. Smith may enter text input into a message box 706 displayed as part of the public communication interface 700. The VHA retrieves the most recently obtained patient temperature and sends the temperature to the care team as a message. All the messages on the public communication thread are viewable by both Dr. Martinez and Dr. Smith, and any other care providers that may be joined to the communication channel for patient ID 1234 as part of the care team for the patient.

In some circumstances, it may be desirable for a care provider to communicate with the one or more VHAs without including other care providers on the communication thread. For example, a care provider may desire to seek out educational information, guidance, confirm or recheck information provided by another care provider, set personalized notifications, or other action that, if sent to the other care providers, may unnecessarily burden or interrupt the other care providers, and/or undermine the confidence of the requesting care provider or other care providers. Accordingly, if a care provider chooses to interact only with the one or more VHAs, the care provider may enter an input requesting to communicate over a private communication thread. For example, Dr. Smith may enter an input (e.g., a touch input or a mouse-based input) selecting the public/private icon 704 or selecting the icon for the VHA (e.g., the icon for Alan). Selection of the appropriate icon (e.g., the public/private icon or the VHA icon) may cause display of a private communication thread, specific to patient ID 1234, where communication between only Dr. Smith (who requested the private communication thread) and the one or more VHAs occurs.

Figure 8:
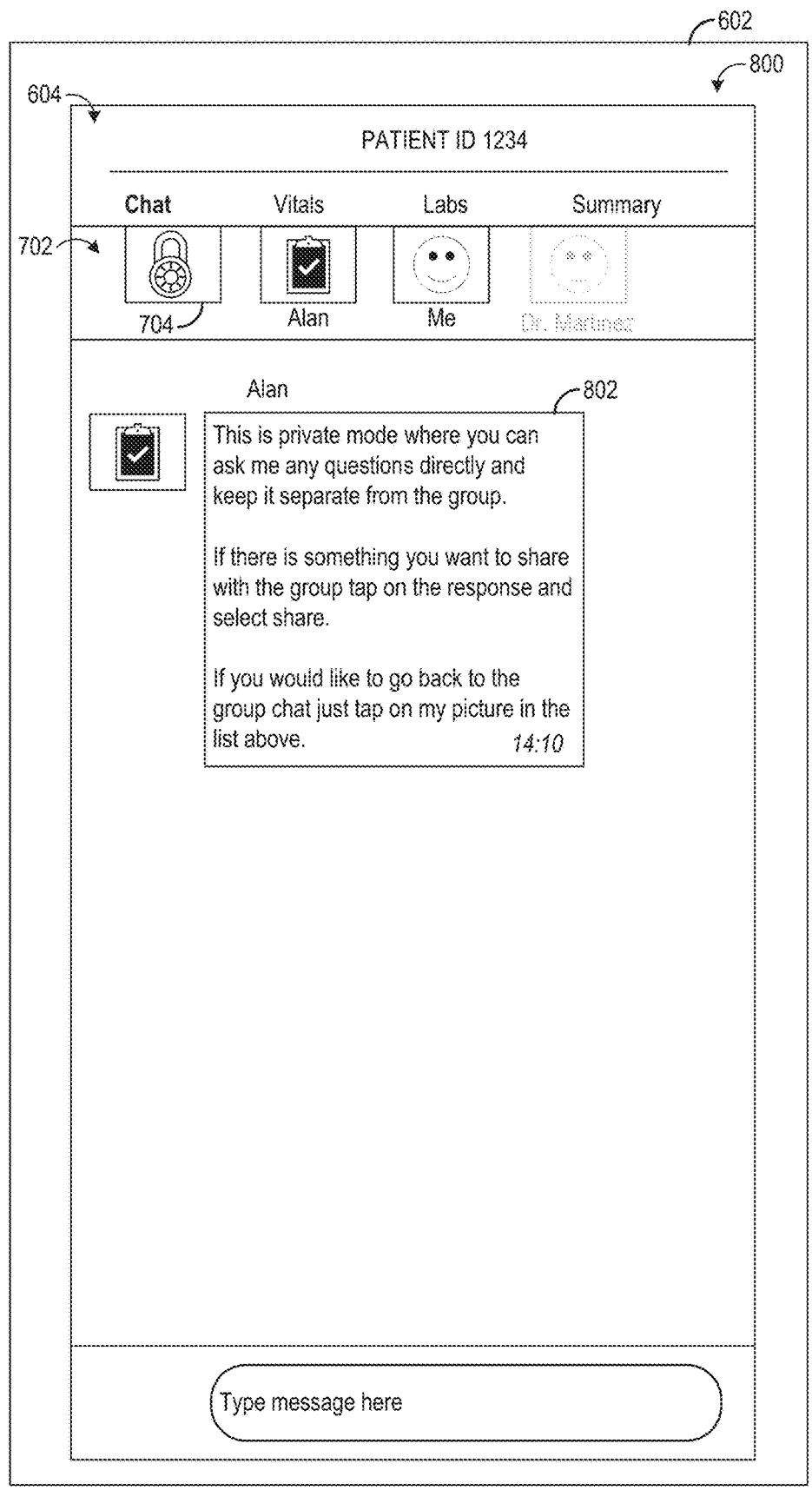
FIGS. 8-10 show an example display device displaying an example private communication thread occurring on a communication channel of the collaborative healthcare system.

Accordingly, in response to a user input requesting to launch a private communication thread, a private communication interface is displayed. FIG. 8 shows a private communication interface 800 of a patient-specific communication channel, via which a private communication thread between a care provider and one or more VHAs may occur. Private communication interface 800 may be displayed on the display device 602. Private communication interface 800 may be displayed in response to a user request to display the private communication thread (e.g., by selecting the Alan icon) and may include the identification header 604 that identifies the patient being discussed/monitored via the communication thread (patient ID 1234 in the illustrated example). The private communication interface 800 also includes the group chat identifier 702, which shows who is joined to the communication thread. The group chat identifier 702 includes the public/private icon 704, which has been adjusted to show a locked padlock, indicating the communication thread is private. The other icons in the group chat identifier 702 include an icon for Alan (the VHA), an icon for Dr. Smith (e.g., "me"), and an icon for Dr. Martinez. However, because the communication thread is private, Dr. Martinez is not included on the communication thread. As a result, the icon for Dr. Martinez is adjusted to be less prominent/visible (e.g., the icon is faded) to indicate that, while Dr. Martinez is included on the public communication thread for patient ID 1234, Dr. Martinez is not included on the private communication thread. Other mechanisms for indicating who is communicating on the private versus public communication threads are possible, such as completely removing the icon(s) for the care provider(s) not included on the private communication thread.

In the illustrated example, Alan outputs a message 802 to Dr. Smith, acknowledging that the private communication thread has been launched. As shown in the message, Alan notifies Dr. Smith that any questions/requests entered via the private communication interface 800 will be kept private and separate from the care provider team. Further, the message indicates that if Dr. Smith chooses, a message on the private communication thread may be shared with the care team and that Dr. Smith may return to the public communication thread via a suitable input (e.g., selecting the icon of the VHA in the group identifier, selecting the public/private icon, or other suitable input).

Figure 9:
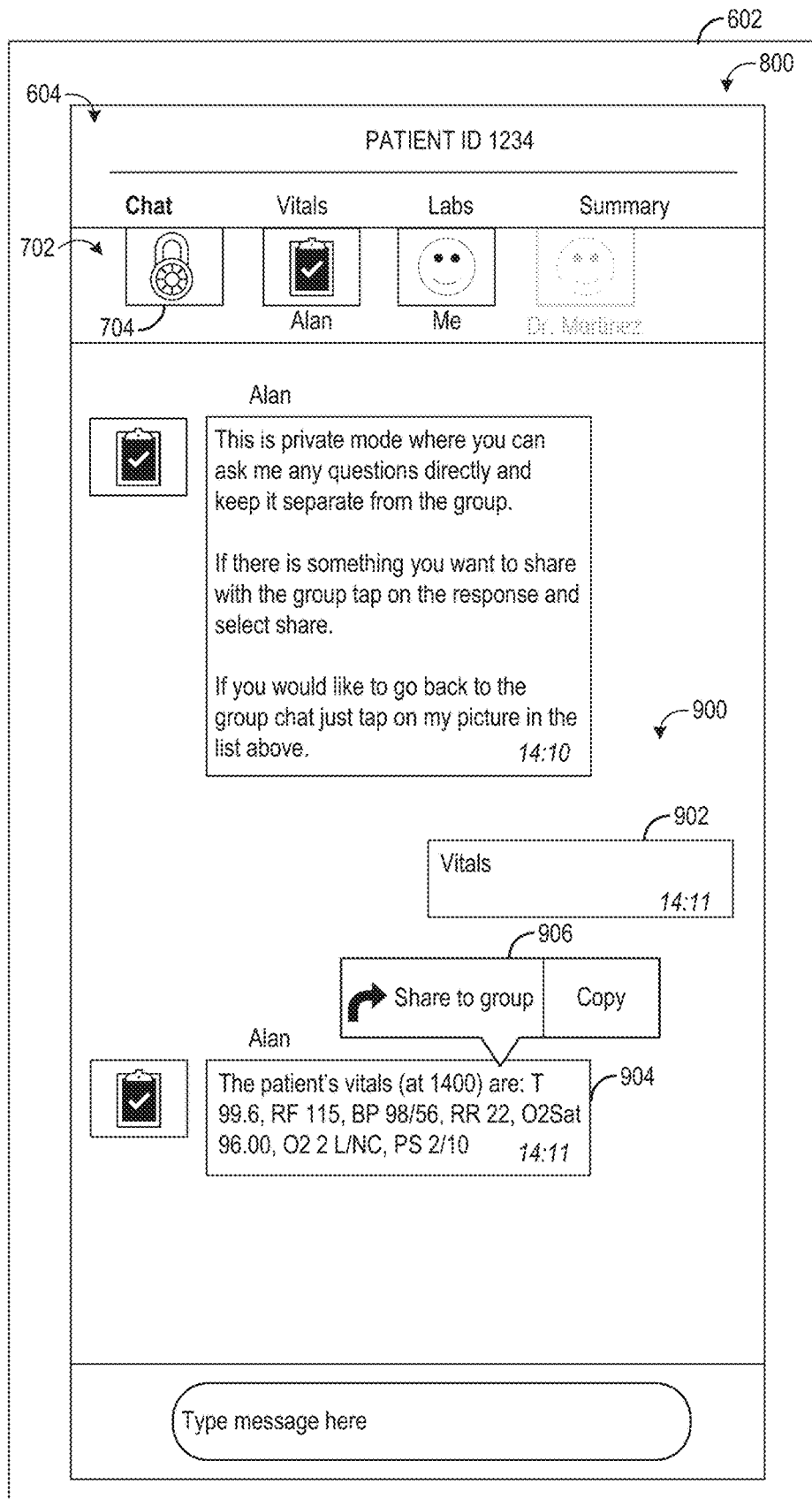

FIG. 9 shows a continuation 900 of the private communication thread between Alan and Dr. Smith occurring on the private communication interface 800. As shown, Dr. Smith asks Alan for the patient's vital signs, at message 902. In response, at message 904, Alan retrieves the patient's most recent vital signs (e.g., measured or otherwise obtained at 14:00) and enters the vital signs as a message 904. Message 902 and message 904 are only visible to Dr. Smith and Alan (e.g., the one or more VHAs) and are not visible to Dr. Martinez or any other care providers. As an example, Dr. Smith may have a tendency to seek out patient updates/ information on a more frequent basis than Dr. Martinez, and Dr. Smith may not want to overburden Dr. Martinez with potentially unnecessary information. Thus, Dr. Smith may choose to receive updates about patient status via the private communication thread.

However, if Dr. Smith thinks that information received on the private communication thread may be of value to Dr. Martinez or other care providers on the care team, Dr. Smith may choose to share the information. For example, upon receiving the most recent patient vital signs via message 904, Dr. Smith may determine that the patient vital signs have changed and that the other care providers (e.g., Dr. Martinez) may benefit from being notified about the patient vital signs. To share the message, an input may be entered selecting message 904 (e.g., a touch input to message 904). In response, an action menu 906 may be displayed. The action menu 906 may include interface control buttons for performing certain actions, including a "share to group" action. Selection of the "share to group" button may result in message 904 being published in the public communication thread for patient ID 1234.

Figure 10:
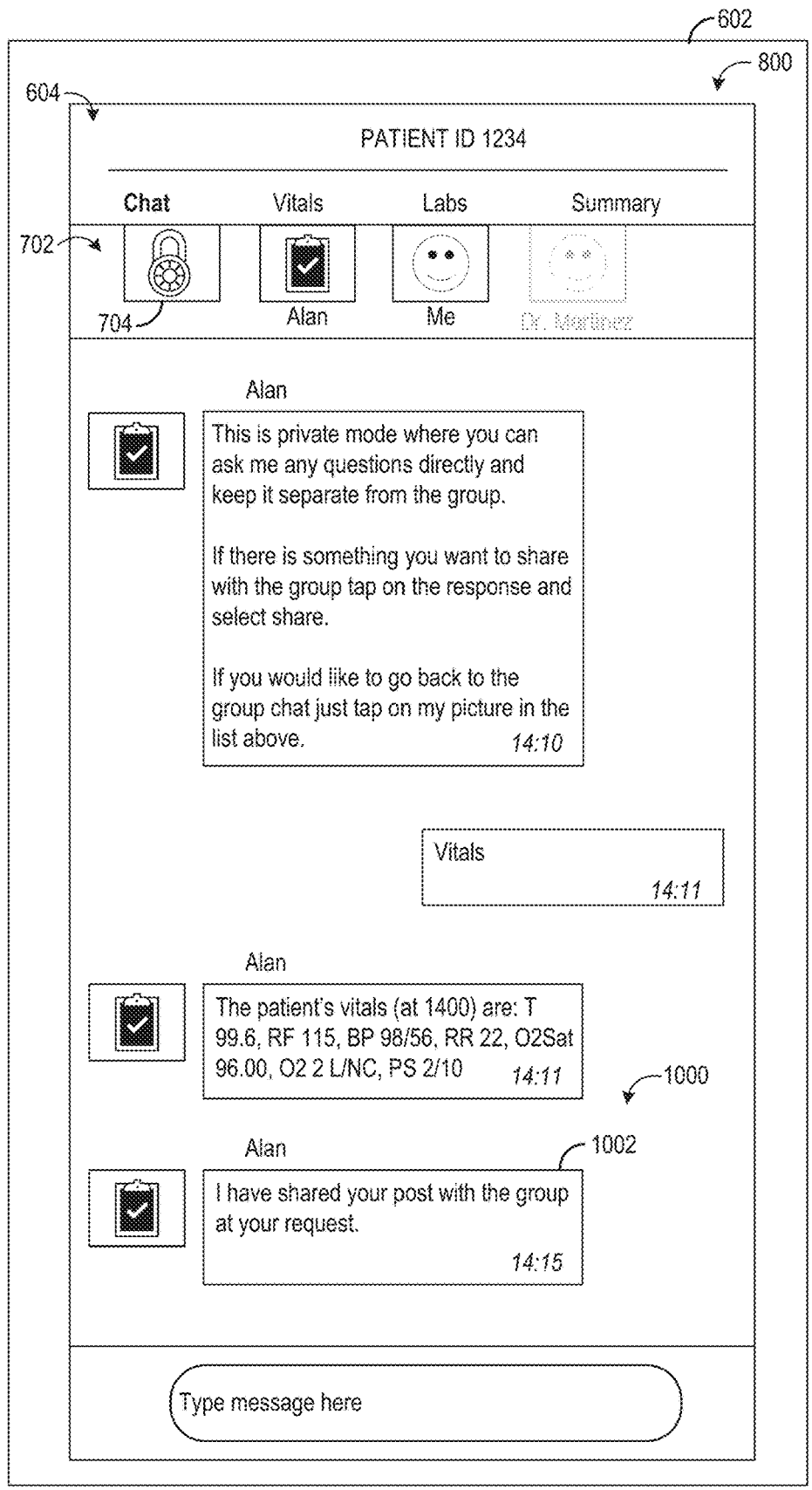

As shown in FIG. 10 (which shows a continuation 1000 of the private communication thread between Alan and Dr. Smith occurring on the private communication interface 800), once the selected message has been published on the public communication thread, the VHA (Alan) may output a message 1002 notifying Dr. Smith that the message has been shared.

Figure 11:
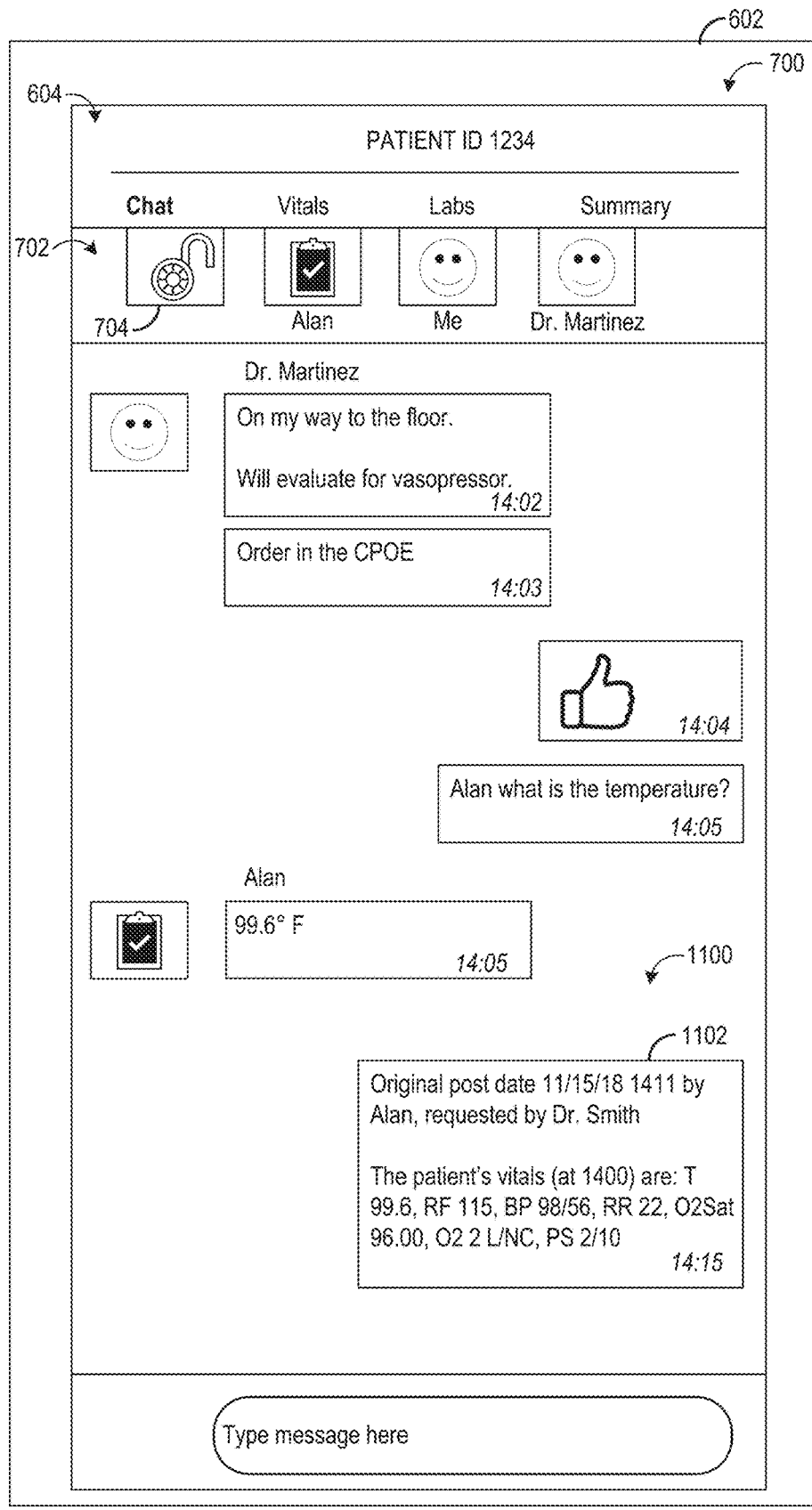

FIG. 11 shows a continuation 1100 of the public communication thread between Alan, Dr. Smith, and Dr. Martinez occurring on the public communication interface 700. For example, Dr. Smith may enter a suitable input (e.g., a touch input to the Alan icon) requesting to view the public communication thread, and in response the public communication interface 700 may be displayed. As shown in FIG. 11, a message 1102 is sent on the public communication thread including the message shared by Dr. Smith from the private communication thread. The message 1102 on the public communication thread includes a notification that the message was shared by Dr. Smith and originally posted by Alan at 14:11. In this way, the other care providers that are a part of the care team for patient ID 1234 may be notified of the patient vital signs presented in the original message sent from Alan on the private communication thread to Dr. Smith, and may also be notified of when the original message was posted, who posted it, and who requested the message be shared.

When sharing a message from the private communication thread to the public communication thread, the one or more VHAs may obtain the most recent patient information available to include in the message, even if the information would be different than the information included in the original message. For example, if a care provider requests, via the private communication thread, to view a trend graph for the patient's heart rate, the one or more VHAs may obtain the heart rate data for the patient (e.g., over the past 12 or 24 hours) and assemble the trend graph based on the heart rate data. If the care provider requests that the heart rate trend graph be shared on the public communication thread, the one or more VHAs may reobtain the heart rate data and assemble a new heart rate trend graph that may or may not match the original heart rate trend graph output on the private communication thread. For example, if a new heart rate measurement were made available after the original heart rate trend graph was assembled, the new heart rate measurement may be included in the new heart rate trend graph. In this way, the care providers may always be provided with the most recent and up to date patient information.

In this way, the computing device provides a specific manner of displaying a limited set of information (e.g., the private communication thread) to the user, rather than using conventional user interface methods to display a generic index/list on a computer that may require the user to step through multiple menus and/or lists of communications and alerts to find the relevant medical information. For example, the private communication interface, via which communication on the private communication thread may be entered and viewed, may be launched from an unlaunched state in response to a user input while the user is viewing the public communication interface. The public-private thread interface link disclosed herein may be advantageous because it avoids a user having to scroll around and switch views multiple times to find desired communication threads, thereby preventing drilling down through many layers to get the desired data/functionality which may be slow, complex, and difficult to learn. The disclosed public-private thread interface link may improve the efficiency of using the computing device by bringing together the medical information most relevant to the user and the communication thread(s) referencing the medical information, while easily allowing the user to switch to from private communication with only a virtual healthcare assistant to public communication with the virtual healthcare assistant and one or more other care providers without actually accessing an electronic medical record or separate interface where patient monitoring data may be displayed. The speed of a user's navigation through various views and windows may be improved because the disclosed link between the public and private communication threads, as well as the disclosed ability to share information from the private communication thread to the public communication thread, saves the user from navigating to an electronic medical record database, opening the database up, and then navigating within the database to enable the medical information of interest to be seen or a function of interest to be activated.

Figure 12:
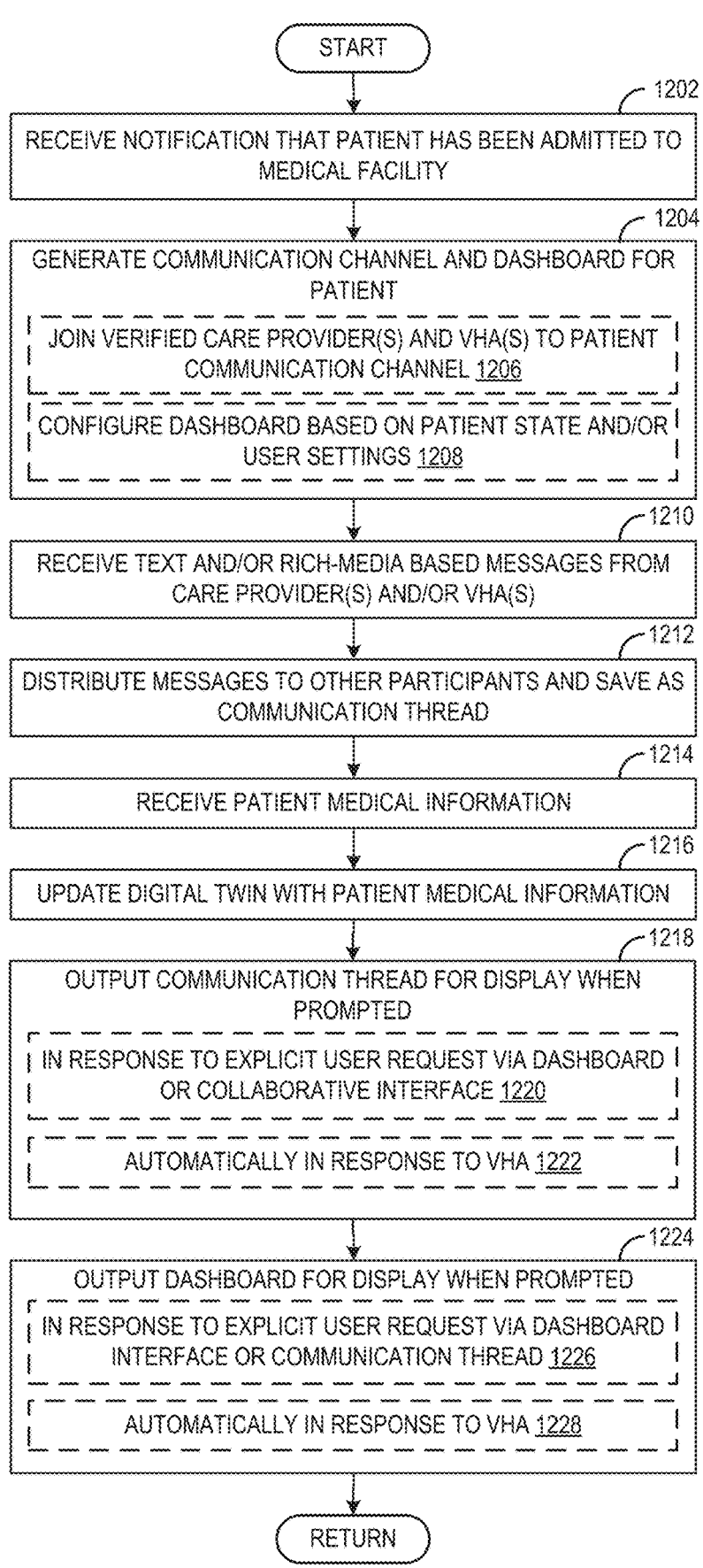
FIG. 12 is a flow chart illustrating an example method for facilitating communication within a collaborative healthcare system.

FIG. 12 is a flow chart illustrating a method 1200 for a collaborative healthcare system serving a medical facility, such as a hospital. Method 1200 may be executed by a processor of a computing device (such as processor(s) 132 of server system 102 of FIG. 1) according to instructions stored on a non-transitory memory of the device (e.g., memory 130 shown in FIG. 1) in combination with the various signals received at the server system from components of the collaborative healthcare system (e.g., patient medical data signals from monitoring devices 120, communication from hospital operational systems 118, etc.) and signals sent from the server system to the care provider devices and/or other system components.

At 1202, method 1200 includes receiving a notification that a patient has been admitted to the medical facility. The notification may be received from the hospital operational systems, and may include a patient identifier, patient state (e.g., the condition for which the patient is being admitted), and care provider information. The care provider information may include identifiers of various care providers (such as doctors and nurses) that are currently attending to the patient.

At 1204, method 1200 includes generating a communication channel including one or more communication threads and a dashboard for the patient. In order to generate the communication channel, verified care providers of the patient (e.g., as indicated by the notification from the hospital operational systems) and one or more virtual healthcare assistants (VHAs) may be joined to the communication channel, as indicated at 1206. The communication channel may facilitate text and/or rich-media based messages to be sent among all the verified care providers and VHAs that are joined to the communication channel. The one or more VHAs may include an EMR VHA, a guideline VHA, a predictive VHA, a listening VHA, a monitoring VHA and/or other VHAs. To join the channel, each VHA may receive a message that a new channel has been opened and the access application (e.g., executing on the server system 102) may add the VHAs to the eligible participants of the channel. Moreover, in some examples, not all available VHAs may be invited to all channels (e.g., a sepsis VHA may not be invited in a non-relevant case or the listening VHA may not be invited due to patient refusal to be monitored by recording).

Generating the dashboard may include configuring the dashboard based on the patient state and/or user settings, as indicated at 1208. As explained previously, a patient dashboard may be a graphical user interface that facilitates display of patient medical information, such as real-time vital signs, medical history, treatment plan, and/or other information. The dashboard may also include relevant/desired messages from the communication thread. Which medical information to display on the dashboard and in what format may be determined based on the patient state (e.g., current medical condition for which the patient is being treated) and/or on user settings, which may be configured by the end-viewer of the dashboard. In this manner, different patients may have different medical information displayed on different dashboards, and different care providers may view different medical information for the same patient, if desired.

At 1210, method 1200 includes receiving text- and/or rich-media-based messages from the participants on the communication channel, including care providers and VHAs. During the course of patient care, care providers may communicate with each other on the communication channel via messages of the communication thread to coordinate care, give care instructions, and/or confirm appropriate care is being carried out. Further, care providers may send requests to the VHAs via the communication thread for various information related to the patient care, including patient medical history, care guidelines, predicted future patient state, recommended lab tests, etc. Further still, VHAs may send notifications via the communication thread of changes in patient state, patient medical history, patient care guidelines, predicted future patient states, lab test status, etc. The messages sent from a care provider may be sent from a care provider device (e.g., device 134) and received at the server system via a suitable connection (e.g., wired or wireless, such as via the Internet). The messages sent from the VHAs may be generated by the VHAs, which may be stored and executed on the server system, the cloud, and/or a remote device. As used herein, messages may refer to any suitable information sent and received on the communication thread, including but not limited to text messages (entered via typing, touch, or stylus input, voice input, or automatically generated by a VHA), images, voice messages (e.g., recordings of voice input), and videos.

At 1212, method 1200 includes distributing the received messages to other participants on the communication channel and saving the received messages as a communication thread. Each message that is sent to the server system may be tagged with various identifiers that identify the sender as well as the patient communication thread to which the message pertains (e.g., the patient identifier). The server system may then send the message to other participants of the communication channel, e.g., the care providers and/or VHAs that did not send the original message, and save the message as part of a saved communication thread. The saved communication thread may then be viewed by other users at other times, retrieved in response to a user request to view some or all of the communication thread, etc. However, in some examples, the device from which the original message was sent (e.g., the care provider device) may send the message to all other participants on the communication channel, and thus the server system may not distribute the message to the other participants.

In some examples, the one or more communication threads may include a public communication thread and a private communication thread. When communication is occurring on a public communication thread, the messages on the public communication thread may be distributed and saved in the manner described above (e.g., all messages on the pubic communication thread may be distributed to all members of the care team for the patient and saved such that the messages may be retrieved by any member of the care team). However, when communication is occurring on a private communication thread, the messages on the private communication thread may only be distributed to the single care provider that initiated the private communication thread (as well as the one or more VHAs joined to the communication channel for the patient). The messages on the private communication thread may be saved and retrieved by only the care provider that initiated the private communication thread. Additional information about the public and private communication threads is presented below with respect to FIG. 13.

At 1214, method 1200 includes receiving patient medical information. The patient medical information may be received from one or more patient monitoring devices that are configured to measure patient state and condition, including sensors that measure vital signs (e.g., blood pressure, heart rate, and blood oxygen level), diagnostic imaging modalities, microphones in proximity to the patient, and so forth. Additionally, the patient medical information may be received from the communication thread. For example, two care providers may be messaging each other on the communication thread and exchanging information relating to the patient, such as visual information (e.g., skin pallor, redness, or yellowness) of the patient that may indicative of patient state. One or more of the VHAs may be configured to parse the message and determine that relevant medical information is being exchanged and then save the medical information as messages within the communication thread.

At 1216, method 1200 includes updating a digital twin of the patient with the medical information. The digital twin may be a digital replica/representation of the patient that is saved at the computing device (e.g., digital twin 108 saved on the server system 102). The digital twin may include patient demographic information, medical history, and other information to provide, to the extent possible, a simulation/representation of the current patient medical state. When new or updated medical information is received, the digital twin may be updated to reflect the most recent patient medical state. The digital twin may be accessed (e.g., by one or more of the VHAs) to retrieve patient medical information, predict future patient states (e.g., simulations may be performed using the information stored in the digital twin to determine the probability of the patient developing a certain condition), identify the most relevant lab tests to be conducted to diagnose a patient condition, and provide appropriate context when retrieving care guidelines.

At 1218, method 1200 includes outputting a communication thread for display when prompted. In an example, the prompt may include an explicit request to view the public communication thread for the patient, entered by selection of an appropriate link/control button on the patient dashboard or selection of the patient's public communication thread from a collaborative interface, as indicated at 1220. For example, a message button may be displayed via the patient dashboard, and selection of the message button may trigger display of the public communication thread for that patient. In another example, a patient link may be selected to launch the public communication thread from a collaborative system interface. In an example, the public communication thread may be output for display automatically in response to a request from one or more of the VHAs, as indicated at 1222. For example, a listening VHA may detect that one or more care providers are discussing a particular piece of the patient's medical history, and the listening VHA may send a portion of the public communication thread that includes reference to the particular piece of medical history to the care provider's device for display. In another example, a VHA may detect that a patient vital sign has reached a level that may indicate a potential urgent patient condition and the VHA may output an alert regarding the vital sign on the public communication channel. In some examples, issue of such an alert may prompt automatic display of the public communication thread on each participant's display device. A private communication thread may only be launched in response to a user request to launch a private communication thread, as explained below with respect to FIG. 13.

At 1224, method 1200 includes outputting the dashboard for display when prompted. In an example, the prompt may include an explicit request to view the dashboard for the patient, entered by selection of an appropriate link/control button on a public or private communication thread or selection of the patient's dashboard from a collaborative interface, as indicated at 1226. For example, as shown in FIG. 2, a link to the dashboard may be displayed in a communication thread, and selecting the link may trigger display of the dashboard for that patient. In an example, the dashboard may be output for display automatically in response to a request from one or more of the VHAs, as indicated at 1228. For example, the listening VHA may detect that a care provider is discussing the patient's current medical state and may automatically output the dashboard for display on the care provider's device so that the care provider may view patient medical information displayed in the dashboard that relates to the current medical state being discussed. Method 1200 then returns.

Figure 13:
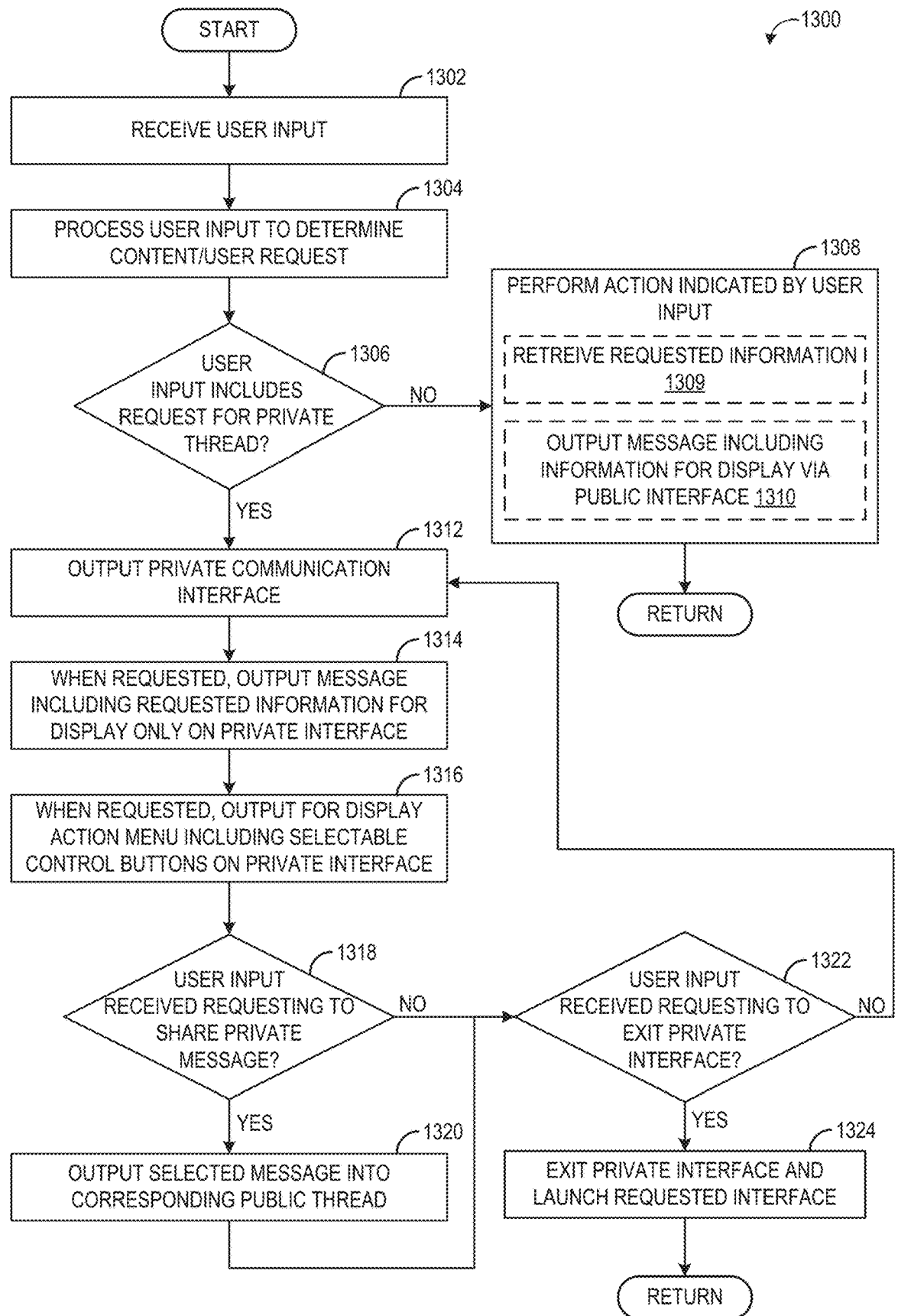
FIG. 13 is a flow chart illustrating an example method for generating and outputting public and private communication threads via the collaborative healthcare system.
Figure 14:
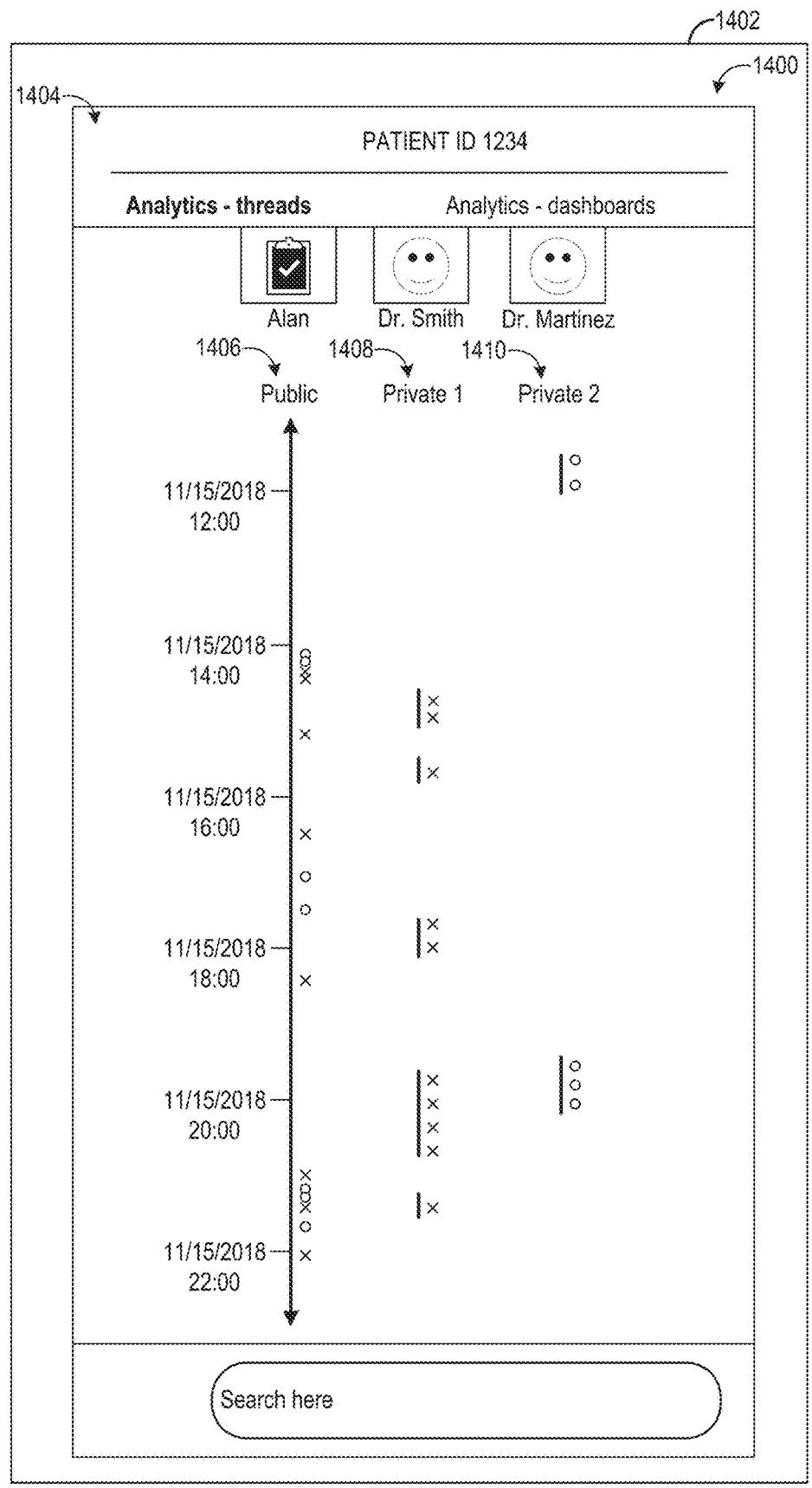
FIG. 14 shows an example display device displaying an example analytics interface visually presenting a plurality of communications threads occurring on the collaborative healthcare system.

FIG. 13 is a flow chart illustrating a method 1300 for launching and displaying public and private communication threads for a patient. Method 1300 may be executed by a processor of a computing device (such as processor(s) 132 of server system 102 of FIG. 1) according to instructions stored on a non-transitory memory of the device (e.g., memory 130 shown in FIG. 1). As explained above with respect to FIG. 1, the server system 102 may store/execute one or more virtual healthcare assistants (VHAs) that are configured to perform certain tasks related to providing medical information of the patient to the one or more care providers attending to the patient, as explained below.

At 1302, method 1300 includes receiving a user input. The user input may be input as a selection of user interface control button or a message from a care provider, via voice or text, and may include patient-specific information in natural language form, in some examples. For example, as explained previously, each patient may have a dedicated communication channel including a public communication thread that facilitates communication among the care providers treating the patient and one or more VHAs, as well as one or more private communication threads that each facilitate communication between one care provider and the one or more VHAs. When a care provider enters an input on the public or private communication thread, the input (e.g., message) may be received at the server system and the input may be processed, via the one or more VHAs, to determine the content of the user input, as indicated at 1304. The one or more VHAs may utilize a speech recognition engine in examples where the user input is a natural language input that is input via voice. As explained previously, the one or more VHAs may be trained to process natural language inputs to determine the content of the input, e.g., determine if the input includes a request for information, and if the content includes a request for information, the one or more VHAs may be trained to determine which patient the care provider is referring to and what information is being requested. In some examples, each VHA may process a received message to understand (in natural language) the intent of the message and determine if the intent of the message includes a task that the VHA is trained/configured to perform. In some examples, the server system may include a central entity configured to understand the intent of the message (e.g., from the natural language of the message)

and determine which VHA is best configured to handle the request. Then, the mapping from intent (and VHAs) to a specific API of a specific VHA is one-to-one, e.g., only one VHA handles a specific intent (or intent-entity combination).

The information request may be an explicit request, where the care provider explicitly asks for certain medical information, such as "please send me the patient's heart rate over the last four hours." In other examples, the request may be implicit. Implicit requests may include assumptions (on the part of the VHAs executing on the server system) that certain medical information may be helpful, such as when a change in patient vital signs is detected, that are not accompanied by an actual request by the care provider.

At 1306, method 1300 determines if the user input includes a request to launch a private communication thread. As explained above with respect to FIGS. 8-10, a private communication thread may be launched in response to a user request (e.g., in response to user selection of a VHA icon, in response to a user voice or text input, etc.). In some examples, the private communication thread may only be launched from a corresponding public communication thread. For example, when a public communication thread for a patient is displayed via a public communication interface (e.g., public communication interface 700 of FIG. 7), a user may enter an input to the public communication interface requesting the private communication thread (for the patient) be launched. In other examples, additionally or alternatively, the private communication thread may be launched via input entered to a dashboard (e.g., dashboard 300 of FIG. 3 and/or vitals interface 600 of FIG. 6) and/or via another mechanism. The request to launch the private communication thread may include, whether implicitly or explicitly, an indication of which patient the private communication thread is specific to.

If the user input does not include a request to launch a private communication thread, for example if the user input includes a request to view or send a message via a public communication thread, view a data set (e.g., a heart rate trend), a request for treatment guidelines or diagnosis guidelines, or if the user input is not directed at the VHA (e.g., the message is intended for another care provider), method 1300 proceeds to 1308 and performs one or more actions as indicated by the user input. For example, if the user input includes a request for a medical information from a patient's EMR, the VHA (e.g., EMR VHA) may retrieve the information from the patient's EMR and output the information as a message in the public communication thread for that patient that is displayed via a public communication interface. Thus, in some examples, performing the one or more actions may include retrieving the requested information, as indicated at 1309, and outputting a message including the information for display via the public communication interface, as indicated at 1310. In other examples, the one or more actions may simply include saving/distributing the message on the public communication thread (e.g., when the user input does not include any requests for information).

If the user input does include a request to launch the private communication thread, method 1300 proceeds to 1312 to output a private communication interface that is specific to a patient, via which the private communication thread is displayed. The private communication interface (e.g., private communication interface 800 of FIG. 8) may include a display area where messages on the private communication thread are displayed, as well as a message box for entering text-based messages to the private communication thread and a group identifier that may include a public/private icon that indicates the communication thread is private. In some examples, the private communication interface may include an indication of who is communicating on the private thread (e.g., icons representing the one or more VHAs on the private communication thread and the care provider on the private communication thread). Further, the private communication interface may, in some examples, include an indication of who is not communicating on the private communication thread (e.g., an icon representing another care provider on the care team for the patient, and hence who would be able to view messages on the public communication thread, where the icon is faded or otherwise visually different than the other icons).

At 1314, method 1300 includes, when requested, outputting a message including requested information for display on only the private communication interface. For example, once the private communication interface is launched, the requesting care provider (e.g., the care provider that requested the private communication thread be launched) may enter natural language user input (e.g., as a text message or as a voice input) requesting patient information (e.g., vital signs, trend graphs, medical history, medications taken, lab results, etc.), care guidelines or protocols, personalized notifications to be set, etc. One or more of the VHAs may process the natural language input to determine the content/intent of the natural language input and retrieve any requested information, format the retrieved information into a message, and output the message including the requested information to the private communication thread. The message may then be viewed by the requesting care provider via the private communication interface. For example, referring to FIGS. 9 and 10, a care provider (e.g., Dr. Smith), upon requesting the private communication thread for a patient be launched, may enter a natural language input requesting to view the patient's vital signs. One or more VHAs (e.g., referred to as Alan in the example of FIGS. 9 and 10) may process the natural language input, determine the intent of the request (e.g., to view the patient's vital signs), retrieve the patient's most recently-measured vital signs, and format the vital signs into a message that is output as part of the private communication thread displayed via the private communication interface.

At 1316, method 1300 includes, when requested, outputting for display on the private communication interface an action menu including selectable control buttons. The request to display the action menu may be entered by a user viewing the private communication thread (e.g., the requesting care provider). The input may include a selection of a message displayed via the private communication interface (e.g., via touch input or other suitable input). The action menu may include one or more actions that may be performed via the private communication interface with respect to the message, such as sharing the message on the corresponding public communication interface, copying the message onto a clipboard for subsequent action (e.g., subsequent pasting into an appropriate text box), or other action.

At 1318, method 1300 includes determining if a user input requesting to share a private message has been received. For example, as explained above, a user may select a private message (e.g., wherein the message is considered private because it is only displayed via the private communication interface and is only viewable by the requesting care provider and the one or more VHAs), which may cause an action menu to be displayed. The user may then select a "share to group" button of the action menu, or enter another appropriate input indicating that the user wants to publish the private message to the public communication thread for that patient. For example, as shown in FIG. 9, an action menu (e.g., action menu 906) may be displayed when a private message (such as message 904) is selected. The user/care provider may select the "share to group" button of the action menu in order to request that the selected private message be shared to the public communication thread.

If a user input requesting to share a private message is not received, method 1300 proceeds to 1322, which will be explained in more detail below. If a user input is received requesting to share a private message, method 1300 proceeds to 1320 to output the selected message into the corresponding public communication thread. For example, as shown in FIG. 11, a shared private message may be formatted into a message that is sent on the public communication thread for the patient, which may then be viewed by all care providers on the care team for the patient via a respective public communication interface. The message may be formatted and sent so that the message appears (to the other care providers on the care team) to have been sent by the requesting care provider.

In some examples, the private message that is selected to be shared may be copied or retrieved as-is and shared to the public communication thread without any modifications. Such an approach may save processing resources and/or time by avoiding the need to re-query the one or more VHAs in order to determine/obtain the information included in the private message. However, patient information is time-sensitive and prone to fluctuations that may have clinical significance. If a private message is shared that includes a patient vital sign showing an improvement in patient condition (e.g., an increase in blood pressure from a previously low blood pressure), but the private message is shared at some later time than the private message was originally generated (e.g., an hour later), the patient condition may have changed. For example, despite having increased an hour before, the patient blood pressure may return to its low level. Thus, if the private message is shared as-is, the other care providers on the care team for that patient may erroneously assume that the patient is improving even if the patient's current blood pressure is still low, which may compromise patient care. Thus, to ensure that only the most up-to-date patient information is shared, when a care provider requests to share a private message, the private message may be generated anew. To do so, the original request for information (e.g., "show me patient vital signs") may be sent to the one or more VHAs again, and the one or more VHAs may obtain the most recently-acquired patient information (e.g., the most recently acquired vital signs) to include in the shared private message. In this way, while the shared private message may be in response to the same request for patient information as the request originally made in the private communication thread, the shared private message may in some examples include different values or parameters of the patient information than the original private message.

At 1322, method 1300 includes determining if user input requesting to exit the private interface is received. The user input requesting to exit the private interface may include a request to view the corresponding public communication interface for the patient, a request to view a vitals interface or dashboard for the patient, a request to view the collaborative interface where other patients' communication threads or dashboards may be viewed, a request to exit the collaborative healthcare environment interfaces altogether, or another request to view another suitable interface. If a request to exit the private communication interface is not received, method 1300 returns to 1312 to continue to display the private communication interface and send/receive private messages on the private communication thread. If a request to exit the private communication interface is received, method 1300 proceeds to 1324 to exit the private communication interface and launch a requested interface (e.g., public communication interface, collaborative interface, etc.) if appropriate. Method 1300 then returns.

While method 1300 was described above as being carried out by processor(s) 132 of server system 102 of FIG. 1 (as an example), it should be understood that at least some of the elements of method 1300 described above may be carried out by processor(s) 132 of server system 102 of FIG. 1 in concert with one or more care provider devices, such as care provider device 134 of FIG. 1. For example, when a message is output for display (e.g., at 1314 of method 1300), the processor(s) 132 of server system 102 may output at least some of the message to the care provider device 134 (e.g., via the one or more VHAs), and the care provider device 134 may then process the received message and display the message. In another example, when the action menu is output for display (e.g., at 1316 of method 1300), the care provider device 134 may output the action menu for display on the care provider device, and then send a notification to the server system 102 of the user selection of a button of the action menu, if needed. For example, if the "share with group" button is selected so that a private message is selected to be shared on a public communication thread, the server system 102 may send the private message to the public communication thread. Further, it is to be understood that the term "public" as used in the present disclosure refers to communication occurring between one or more virtual healthcare assistants and two or more care providers (or least communication occurring between one or more virtual healthcare assistants and one or more care providers that may be viewed at a later time by additional care providers) and does not refer to communication that is available to the public at large. Rather, all communication occurring via the collaborative healthcare system described herein is only accessible by authorized individuals.

Method 1300 as described above includes a public communication thread between one or more VHAs and all care providers on a care team of a patient, and further describes one private communication thread between one care provider on the care team and the one or more VHAs. However, respective private communication threads may be established between the one or more VHAs and any requesting care provider. As such, there may be multiple, separate private communication threads specific to a single patient. Accordingly, for a given patient monitored by the collaborative healthcare system described herein, a communication channel may be initiated that includes a dashboard, a public communication thread, and, when requested, one or more private communication threads. Some patients, depending on the condition being monitored, may have a relatively high number of care providers assigned to the patient's care team, e.g., one or more doctors, nurses, medical assistants, specialists (e.g., anesthesiologists), and so forth. Thus, over the course of a duration where the patient is monitored/treated via the collaborative healthcare system, many communication threads may be initiated and maintained that are specific to the patient. In some examples, each thread (whether public or private) may be saved in a suitable storage location (e.g., in memory 130 of server system 102 of FIG. 1), which may allow authorized users (e.g., administrators) to view the threads at a later time. The ability to go back and view saved threads may allow care providers and/or administrators to identify the effectiveness of such threads in improving patient care, determine which care providers utilize the communication threads and which care providers do not, extract additional training datasets for training the virtual healthcare assistants, and other functions. However, the large number of threads, which may span days or weeks depending on the length of the patient's stay in the medical facility, may make it difficult for a user to effectively analyze the different communication threads. For example, if a patient has six care providers on his or her care team, and each care provider sends messages on both the public communication thread and a respective private communication thread, establishing correlation between information being exchanged on the various communication threads and patient care/condition may be challenging, as it may be time consuming and difficult to manually read through the communication threads, align different communication threads with different patient events, and so forth.

Accordingly, the collaborative healthcare system described herein (e.g., the system 100 of FIG. 1) may be configured to perform analytics on the communication threads in order to assist users in extracting additional information from the communication threads that may be useful for care optimization, virtual healthcare assistant training, and so forth. In some examples, the collaborative healthcare system (e.g., server system 102) may be configured to generate and output graphical user interfaces that visually depict all the different communication threads that may have occurred or are ongoing for a selected patient. FIG. 14 shows an example of one such graphical user interface, referred to as an analytics interface 1400 that may be displayed on a display device 1402. Display device 1402 may include a screen on which the analytics interface is displayed and may be coupled to and/or included as a part of a computing device, such as a computing device that is included as part of hospital operations systems 118 shown in FIG. 1. The display device 1402 may be coupled to and/or included as part of a computing device accessible by an administrator of the collaborative healthcare system, at least in some examples.

Analytics interface 1400 includes an identification header 1404, which may indicate that the information viewable by analytics interface 1400 is specific to a selected patient (herein, patient ID 1234). The identification header 1404 may also include different tabs that may be selected to display different types of analytics. As shown, the analytics-threads tab has been selected, and thus analytics interface 1400 is displaying analytics related to communication threads for patient ID 1234. The displayed analytics illustrated in FIG. 14 include three timelines. A first timeline 1406 shows public messages sent by the care providers to the public communication thread for patient ID 1234. A second timeline 1408 shows private messages sent by Dr. Smith on a first private communication thread for patient ID 1234, and a third timeline 1410 shows private messages sent by Dr. Martinez on a second communication thread for patient ID 1234. Messages sent by Dr. Smith are indicated by an x, and messages sent by Dr. Martinez are indicated by a circle. The first timeline 1406 (for the public communication thread) is shown as occurring in a continuous (e.g., non-interrupted) manner, as the public communication thread is considered open/established at all times over the duration depicted in FIG. 14. Time is shown along the y-axis, with time labeled at consistent intervals (e.g., two hour intervals).

The second and third timelines are not continuous and are shown only where interactions between a respective care provider (e.g., Dr. Smith or Dr. Martinez) and the one or more VHAs (e.g., Alan) on the private communication threads are actively ongoing. For example, Dr. Martinez may request that the second private communication thread be launched at just prior to 12:00 on Nov. 15, 2018, and may send two messages on the second private communication thread to Alan (e.g., the VHA). Once Dr. Martinez exits the second private communication thread (e.g., by exiting out of the private communication interface via which the second private communication thread is displayed), the second private communication thread may be considered paused, and hence is not shown on the third timeline until the next time Dr. Martinez launches the second private communication thread (e.g., at approximately 19:30). Each of the timelines shown in FIG. 14 are time-aligned.

A user viewing analytics interface 1400 may make suitable observations about the communication occurring over the three communication threads shown in FIG. 14. As one example, Dr. Smith interacts more frequently with the first private communication thread than Dr. Martinez interacts with the second private communication thread. This difference in interaction with the private communication threads may suggest that Dr. Martinez is more experienced (e.g., in providing care) than Dr. Smith, that Dr. Smith is more comfortable with or more aware of the benefits of interacting with the one or more VHAs, that the two care providers have different care roles, or other observations. An administrator may use this information to provide more training on the value of the one or more VHAs to Dr. Martinez, for example. As another example, a user may observe that at around 20:00, both Dr. Smith and Dr. Martinez were interacting with the one or more VHAs on the respective private communication threads, and that once both private communication threads were paused, both Dr. Martinez and Dr. Smith sent multiple messages on the public communication thread. This may suggest a significant event was occurring to the patient at that time.

As another approach, a user may desire to gather all information related to a specific patient event, such as an episode of lowered blood pressure known to have occurred from approximately 20:00 until 22:00. By time-aligning and simultaneously displaying visual indications of each of the different communication threads, the user may identify which communication threads were active and at what specific times over the course of the patient event and then request the identified communication threads at those times for further analysis. As one non-limiting example, a user may drill down to each communication thread in order to view the messages sent and received at those times via the analytics interface 1400. For example, a user may "zoom in" on the interface at the timelines between 20:00 and 22:00, which may cause additional detail to be displayed, such as the actual messages sent and received on each thread at that time.

Other information may be displayed via analytics interface 1400 that is not shown in FIG. 14, such as messages sent by Alan. As another example, the message indicators shown in FIG. 14 may be coded (e.g., color coded) to indicate if the message was sent to another care provider or to Alan, whether the message included a request for patient information, a request for care guidelines, or a request to set a notification alert, and so forth. As a still further example, significant patient events (e.g., one or more vital signs meeting a threshold condition, such as blood pressure dropping or increasing by a threshold amount) may be annotated on the first timeline or may be presented via a separate timeline, which may assist in quickly correlating communication on the various communication threads and specific patient events.

The technical effect of generating communication channels including communication thread-dashboard pairs for each patient is to facilitate communication among care providers of the patient and allow virtual healthcare assistants to provide information retrieval and patient monitoring duties. By doing so, care provider work load may be reduced, communication among care providers may be increased to avoid redundant or missed care of the patient, and the communication occurring on the channel may be saved in a central location accessible by the care providers. By saving the communication on the channel, patient medical state, care decisions, and more may be viewable at a later time in context. The saved communication on the communication channel may be used to auto-populate medical records, reports, or other forms, and may be available for larger-scale (e.g., hospital-wide) analytics on treatment guidelines and patient outcomes. By facilitating both public and private communication threads, the system described herein may allow care providers to view relevant patient medical information in a public or private forum, which may increase care provider education, access to relevant patient data, and enhance patient care while reducing information overload or alarm-style fatigue for other care providers. Further, by allowing a care provider to directly access relevant and/or curated patient medical information on demand from a communication thread, unnecessary navigation through varying layers of menus to reach desired patient information may be reduced or avoided.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a display; and
a computing device operably coupled to the display and storing instructions executable to:
output, to the display, a public communication thread including communication among two or more care providers monitoring a patient and a virtual healthcare assistant, the public communication thread specific to the patient; wherein the communication among the two or more care providers includes one or more messages sent from the first care provider to one or more additional care providers of the two or more care providers; and
responsive to a request from a first care provider of the two or more care providers, output, to the display, a private communication thread including communication only between the first care provider and the virtual healthcare assistant, the private communication thread specific to the patient and including a visual indication of which care providers are not communicating on the private communication thread,
wherein the request is provided through at least one of: the display, and the computing device.

2. The system of claim 1, wherein the instructions are executable to:
upon outputting the private communication thread to the display, receive a natural language user input, input via text or voice;
process, with the virtual healthcare assistant, the natural language user input to determine a user request;
in response to determining that the user request includes a request for patient information, retrieve the patient information and output, to the display, a private message on the communication thread including the requested patient information.

3. The system of claim 2, wherein the instructions are executable to, responsive to a user input selecting the private message, output, to the display, an action menu, the action menu including one or more control buttons.

4. The system of claim 3, wherein the private message is displayed when the public communication thread is in an unlaunched state, and wherein the instructions are executable to, responsive to receiving a user input selecting a first control button of the one or more control buttons, publish the private message in the public communication thread.

5. The system of claim 4, wherein outputting the private message on the private communication thread includes only sending the private message to one or more devices associated with the first care provider, and wherein publishing the private message to the public communication thread includes sending the private message to the one or more devices associated with the first care provider and one or more additional devices associated with one or more additional care providers of the two or more care providers.

6. The system of claim 4, wherein the private message on the private communication thread includes the patient information retrieved at a first point in time, and wherein publishing the private message to the public communication thread includes retrieving updated patient information obtained at a second, later point in time and replacing the patient information with the updated patient information.

7. The system of claim 2, wherein the virtual healthcare assistant is trained to process the natural language user input to determine the user request, the training based on one or more deep learning models that map a plurality of natural language inputs to intents and entities, the intents including a plurality of user requests and the entities including a plurality of actions to be performed for the plurality of user requests.

8. The system of claim 1, wherein the instructions are executable to output the public communication thread on a public communication interface and to output the private communication thread on a private communication interface.

9. The system of claim 8, wherein the public communication interface includes a public/private icon having a first visual appearance to indicate that the public communication thread is being displayed and wherein the private communication interface includes the public/private icon having a second visual appearance to indicate that the private communication thread is being displayed.

10. The system of claim 8, wherein the public communication interface includes a plurality of chat icons, including a first chat icon associated with the virtual healthcare assistant and two or more second chat icons each associated with a respective care provider of the two or more care providers, and wherein the private communication thread is output for display in response to a user input selecting the first chat icon.

11. A method, comprising:
  generating a communication channel for access by two or more care providers monitoring a patient and a virtual healthcare assistant, comprising a dashboard and a public communication thread, the communication channel specific to a patient;
  distributing public text- and/or rich media-based messages between two or more care providers monitoring the patient and a virtual healthcare assistant on the public communication thread, at least a portion of the messages on the public communication thread including medical data specific to the patient, all public messages on the public communication thread viewable by all care providers joined to the communication channel;
  receiving a request, from a first care provider of the two or more care providers, to launch a private communication thread; and
  in response to the request, distributing private text- and/or rich media-based messages between only the first care provider and the virtual healthcare assistant on the private communication thread, all private messages on the private communication thread only viewable by the first care provider; wherein the private communication view includes a visual indication of which care providers are not communicating on the private communication thread.

12. The method of claim 11, wherein a first private message on the private communication thread includes one or more patient medical parameters retrieved by the virtual healthcare assistant, the one or more patient medial parameters measured at a first point in time.

13. The method of claim 12, further comprising receiving a request to share the first private message to the public communication thread, and in response, retrieving, via the virtual healthcare assistant, one or more updated patient medical parameters measured at a second, later point in time and distributing, on the public communication thread, a first public message including the updated patient medical parameters.

14. The method of claim 13, wherein the first public message includes a notification that the first public message is a reposting of the first private message.

15. The method of claim 11, wherein the private communication thread is a first private communication thread, and further comprising:
  receiving a second request, from a second care provider of the two or more care providers, to launch a second private communication thread; and
  in response to the request, distributing private text- and/or rich media-based messages between only the second care provider and the virtual healthcare assistant on the second private communication thread, all private messages on the second private communication thread only viewable by the second care provider.

16. The method of claim 15, further comprising:
  in response to a third request, outputting, for display on a display device, a graphical user interface including a plurality of time-aligned timelines, each timeline visually indicating communication occurring on each of the public communication thread, the first private communication thread, and the second private communication thread.

* * * * *